United States Patent
Black et al.

[11] Patent Number: 5,988,230
[45] Date of Patent: *Nov. 23, 1999

[54] DUAL CHAMBER DISPENSING CARTRIDGE REFILLING DEVICE

[75] Inventors: Kevin L. Black, Redmond, Wash.; Frederick J. Turk, St. Paul, Minn.; Bruce R. Broyles, Oakdale, Minn.; Darin J. Meyertholen, Woodbury, Minn.; John W. Dubbe, Oakdale, Minn.; James D. Christoff, Birchwood, Minn.

[73] Assignee: Minnesota Mining & Manufacturing Co., St. Paul, Minn.

[*] Notice: This patent is subject to a terminal disclaimer.

[21] Appl. No.: 08/938,036

[22] Filed: Jul. 18, 1997

Related U.S. Application Data

[63] Continuation-in-part of application No. 08/558,844, Nov. 15, 1995, Pat. No. 5,651,397.

[51] Int. Cl.$^6$ ...................................................... B65B 1/04
[52] U.S. Cl. ................................ 141/18; 144/25; 144/27; 144/237; 144/247; 144/346; 285/124.1
[58] Field of Search .................................... 141/9, 18, 25, 141/27, 99, 234, 237, 242, 247, 383, 384, 346; 285/131.1, 137.11, 124.1; 92/151

[56] References Cited

U.S. PATENT DOCUMENTS

| | | | |
|---|---|---|---|
| 4,199,081 | 4/1980 | Mason | 222/43 |
| 4,274,453 | 6/1981 | Lee | 141/1 |
| 4,421,146 | 12/1983 | Bond et al. | 141/349 |
| 4,434,820 | 3/1984 | Glass | 141/2 |
| 4,469,153 | 9/1984 | Morrisette | 141/364 |
| 4,538,920 | 9/1985 | Drake | 366/177 |
| 4,551,135 | 11/1985 | Gorman et al. | 604/82 |
| 4,750,532 | 6/1988 | Grothoff | 141/27 |
| 4,974,756 | 12/1990 | Pearson et al. | 222/562 |
| 5,020,693 | 6/1991 | Ernst et al. | 222/137 |
| 5,064,098 | 11/1991 | Hutter, III et al. | 222/137 |
| 5,080,493 | 1/1992 | McKown et al. | 366/177 |
| 5,092,492 | 3/1992 | Centea | 222/137 |
| 5,137,181 | 8/1992 | Keller | 222/134 |
| 5,236,108 | 8/1993 | House | 222/541 |
| 5,289,949 | 3/1994 | Gentile | 222/137 |
| 5,304,165 | 4/1994 | Haber et al. | 604/411 |
| 5,333,670 | 8/1994 | Brandy et al. | 164/364 |
| 5,335,827 | 8/1994 | Gentile | 222/137 |
| 5,651,397 | 7/1997 | Black et al. | 141/18 |

FOREIGN PATENT DOCUMENTS

| | | |
|---|---|---|
| 0 539 074 A1 | 4/1993 | European Pat. Off. . |
| WO 94/14698 | 7/1994 | WIPO . |
| WO 95/22941 | 8/1995 | WIPO . |

*Primary Examiner*—David J. Walczak
*Assistant Examiner*—Timothy L. Maust
*Attorney, Agent, or Firm*—James D. Christoff

[57] ABSTRACT

A device for consolidating compositions contained in partially filled dual chamber dispensing cartridges includes a body having a pair of passages, and first and second couplers for connecting the body to first and second dual chamber dispensing cartridges. Once the device is connected to two cartridges, an applicator is connected to one of the cartridges and is used to expel any remaining compositions in such cartridge to chambers of the other cartridge. The contents of several partially empty cartridges can be consolidated in this manner so that a subsequent dispensing operation need not be interrupted to replace cartridges.

29 Claims, 15 Drawing Sheets

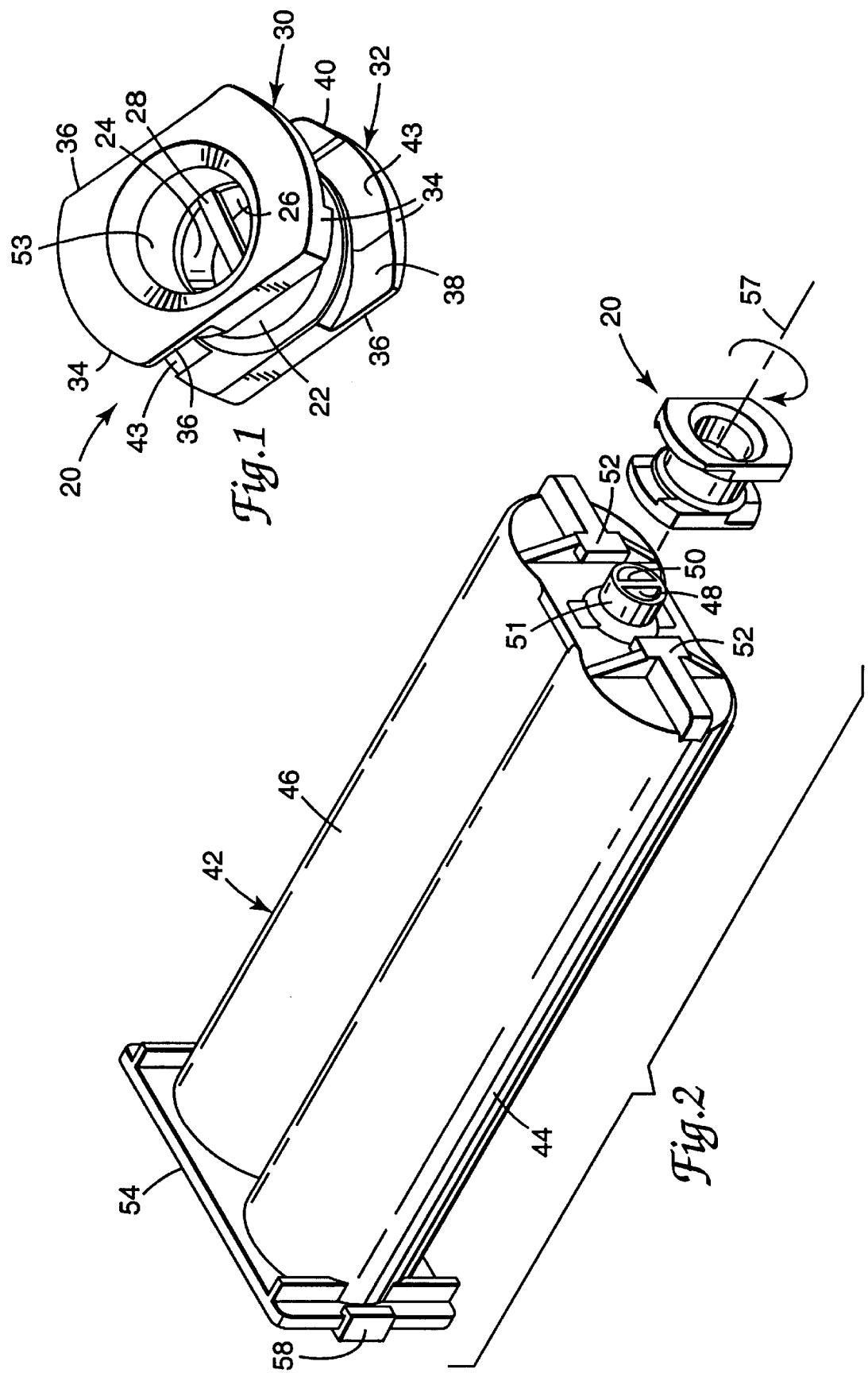

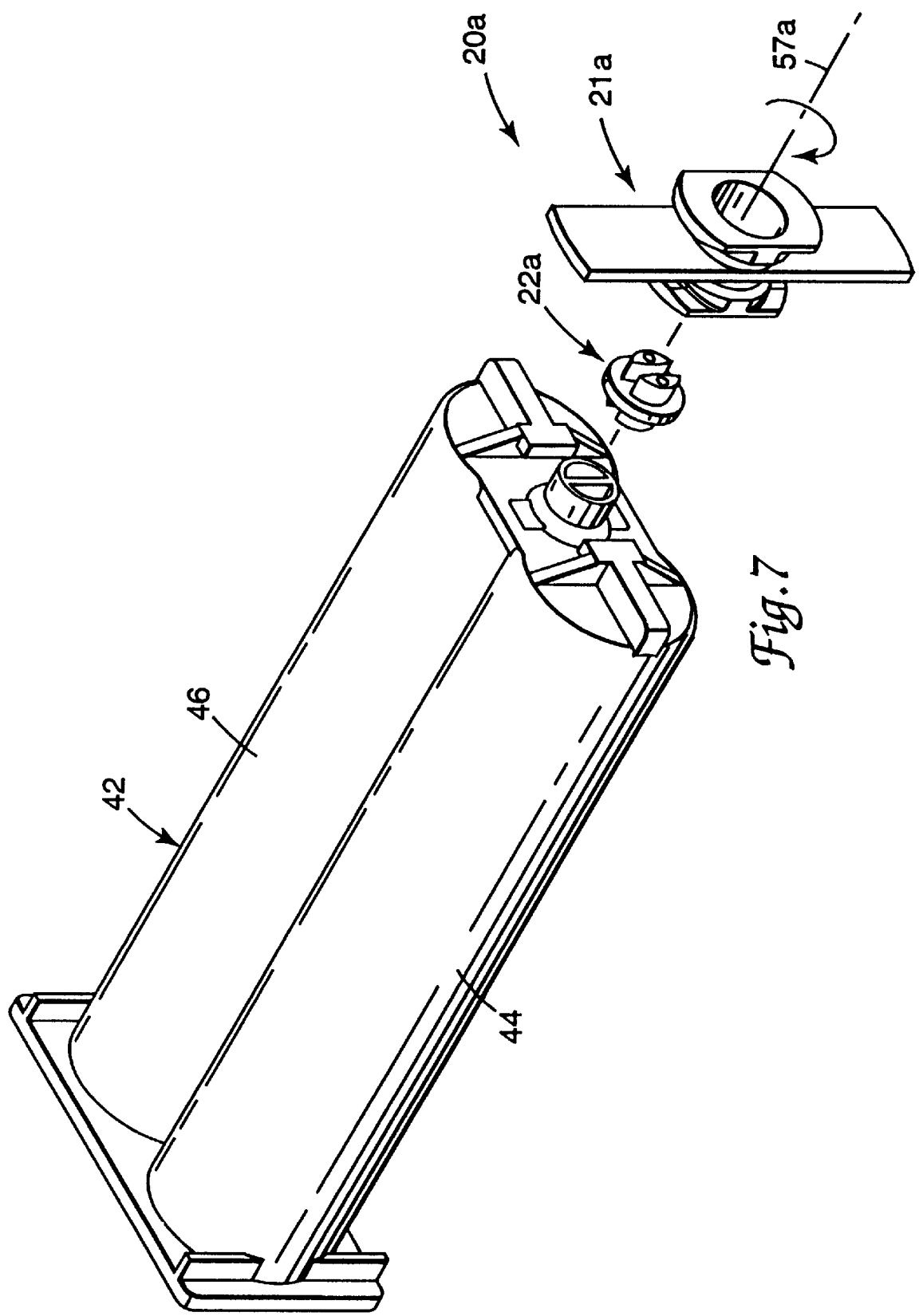

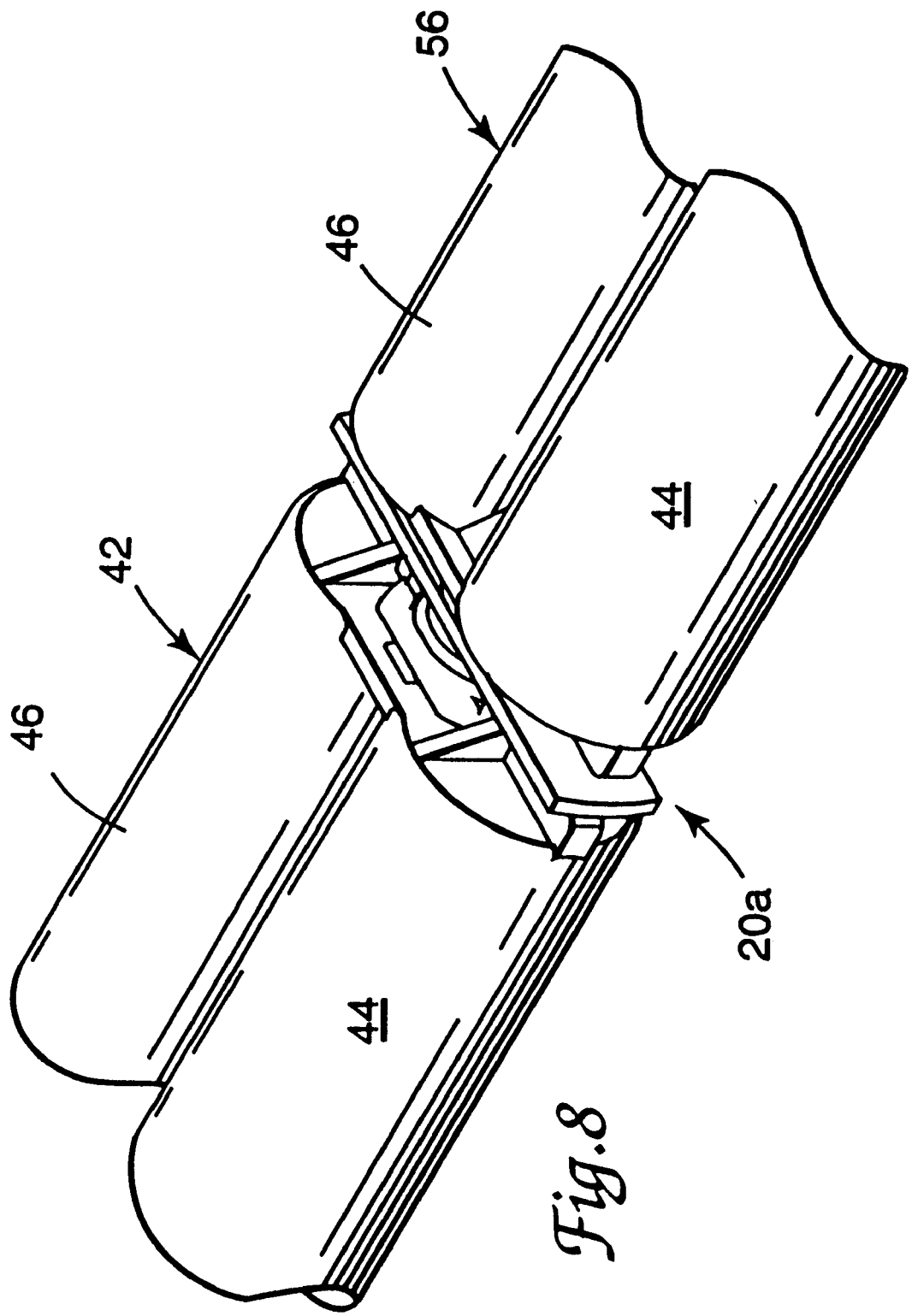

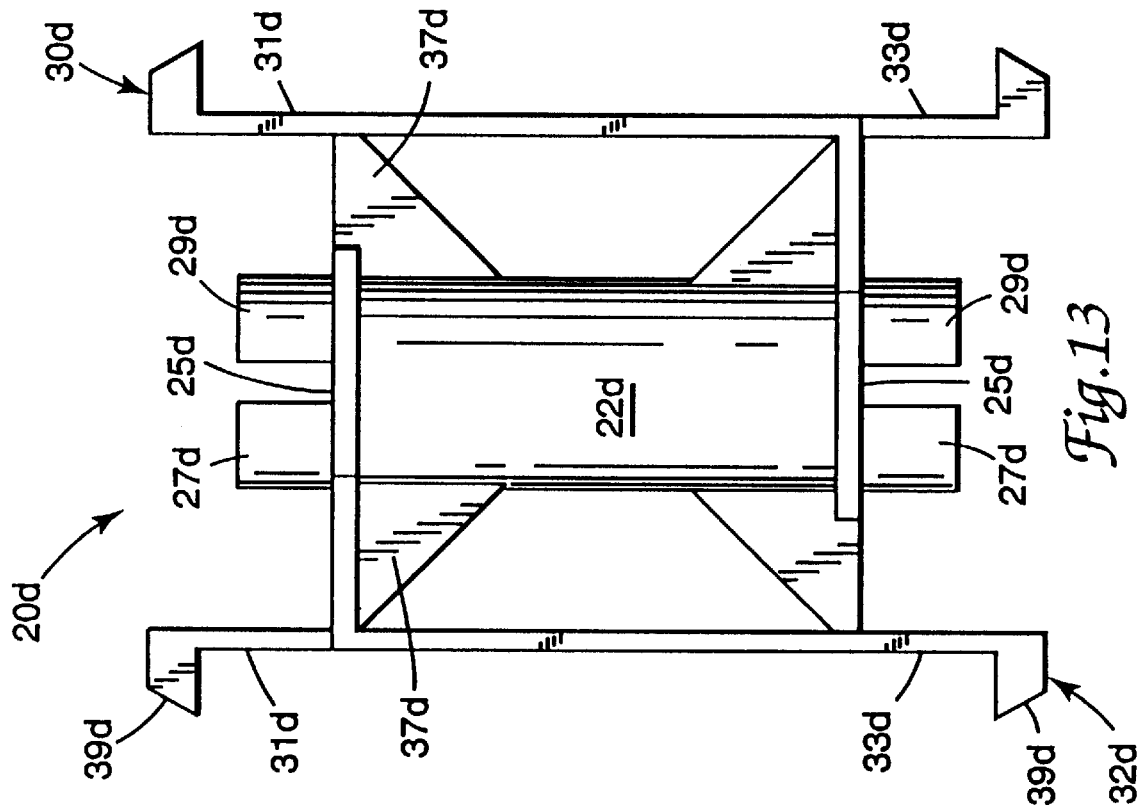
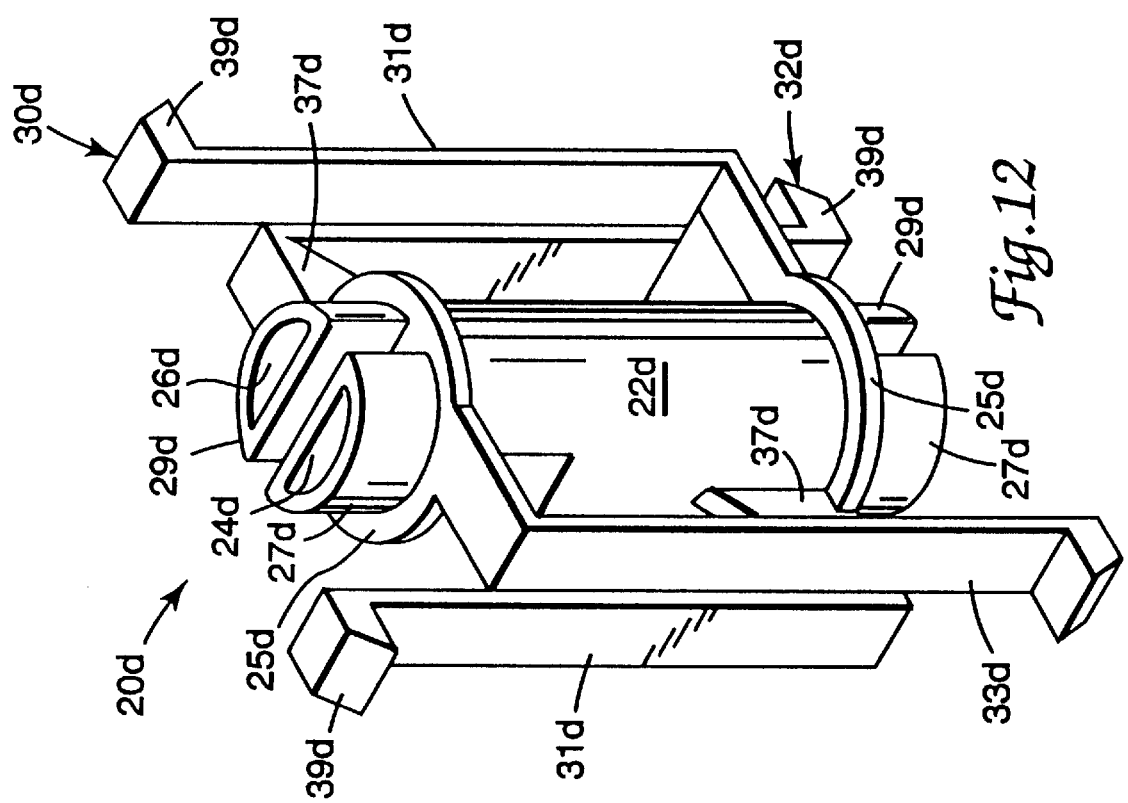

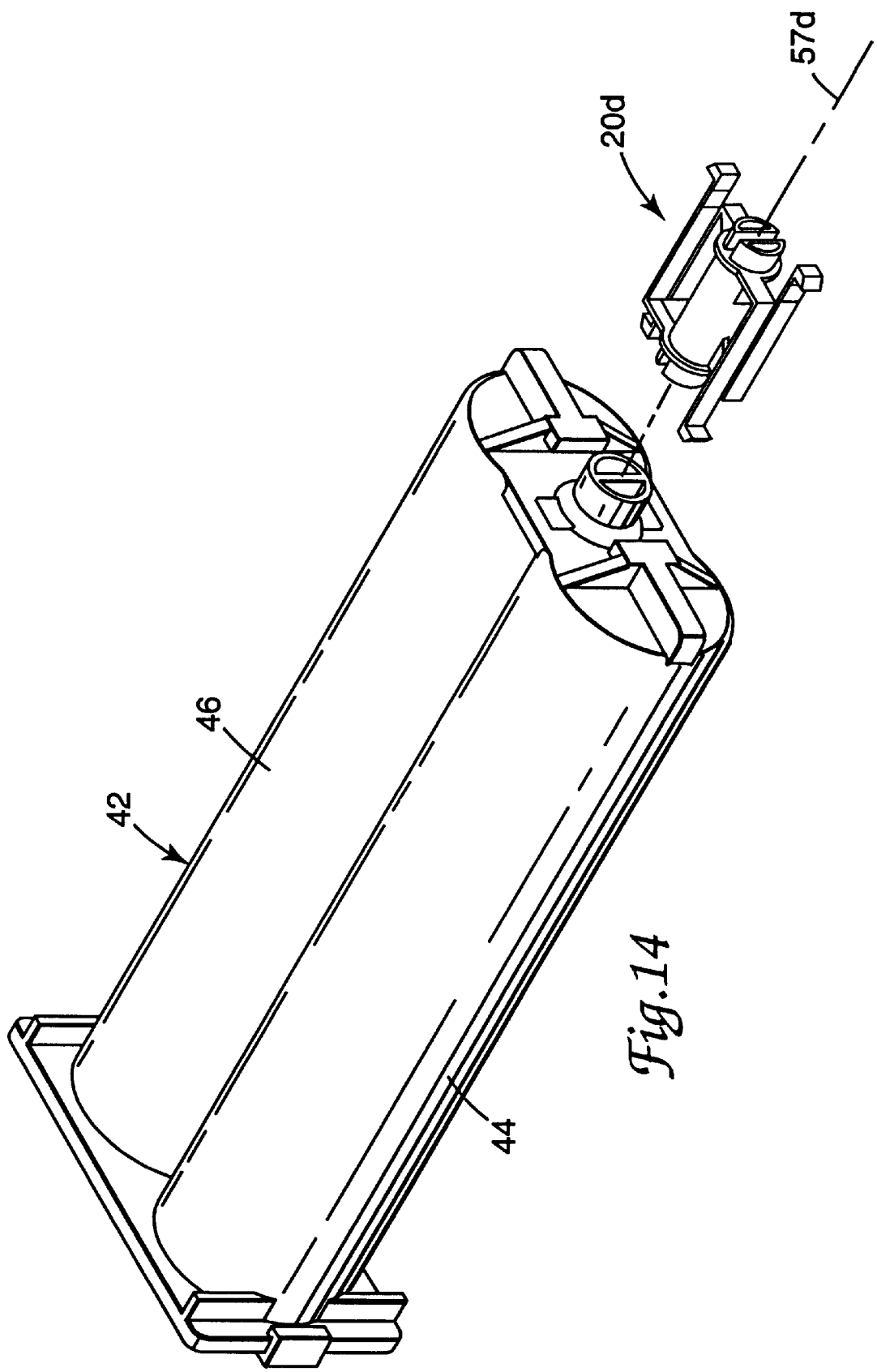

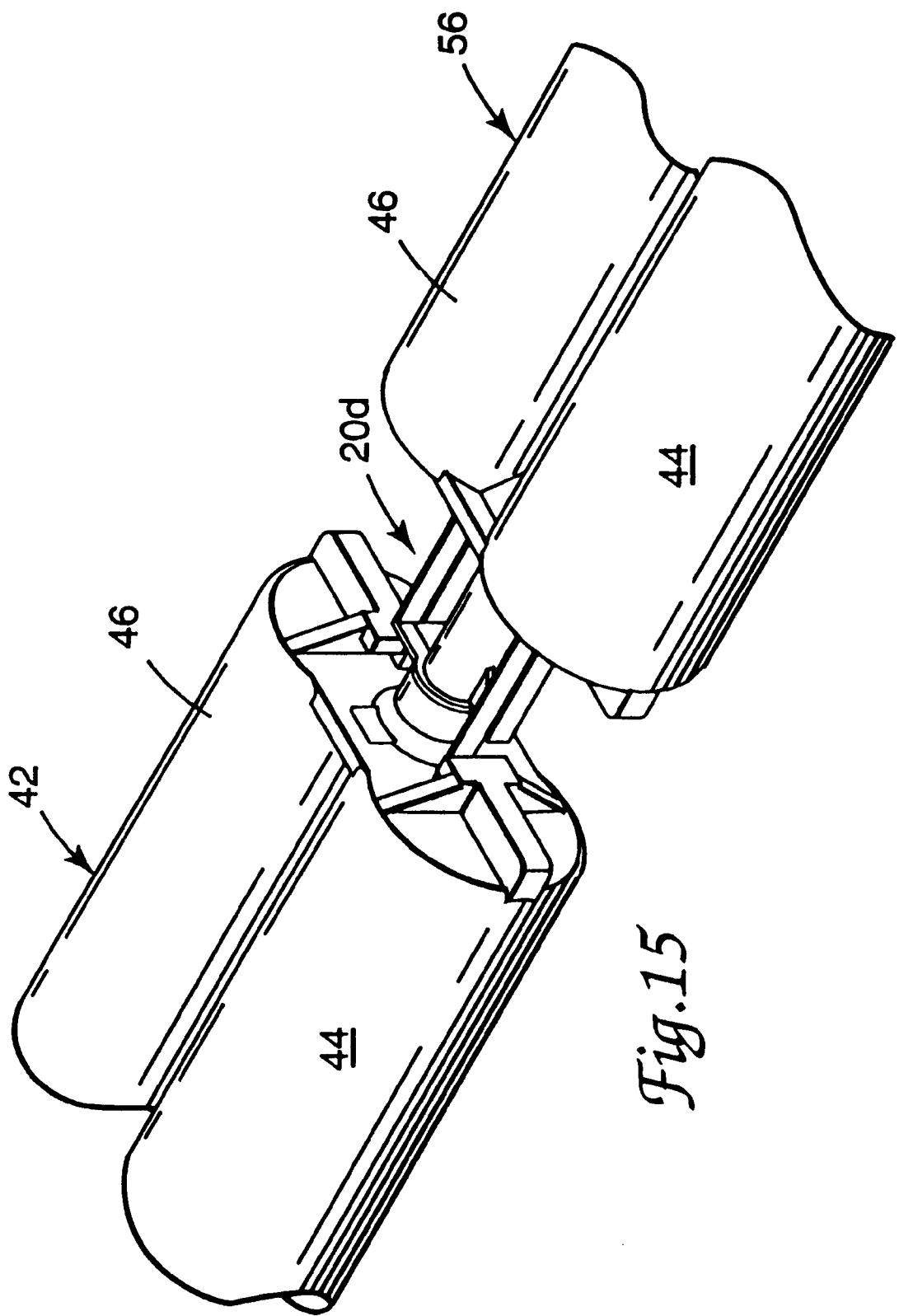

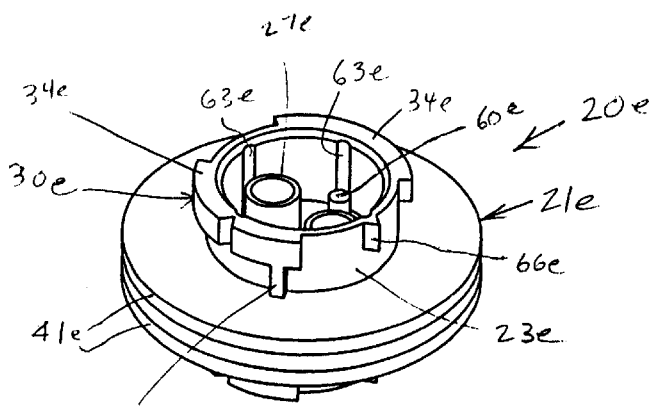
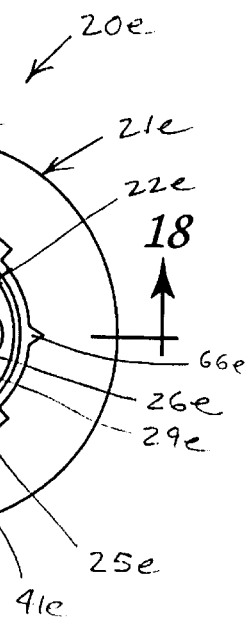
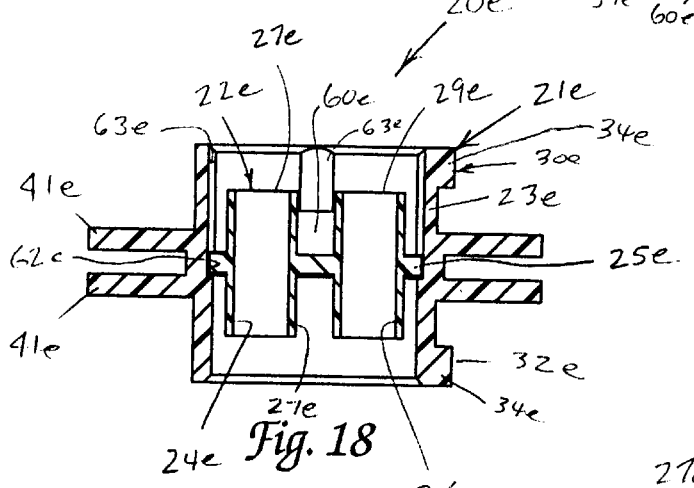
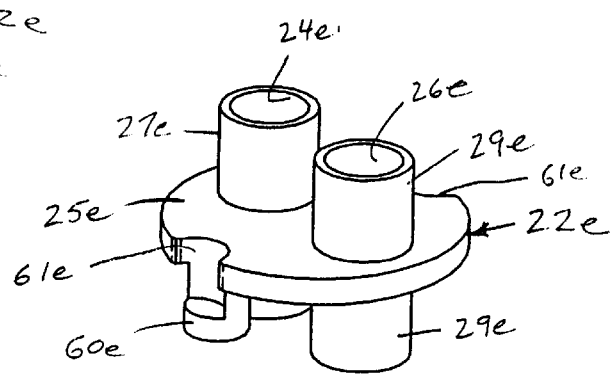

DUAL CHAMBER DISPENSING CARTRIDGE REFILLING DEVICE

This application is a continuation-in-part of U.S. Ser. No. 08/558,844 filed Nov. 15, 1995, now U.S. Pat. No. 5,651,397.

BACKGROUND OF THE INVENTION

1. Field of the Invention

This invention relates to a device for refilling or partially refilling a dual chamber dispensing cartridge used to contain and dispense two components of plural component material such as epoxies or dental impressioning material.

2. Description of the Related Art

Dual chamber dispensing systems are widely used for dispensing material that is made of two components or compositions. Examples of such material in the fields of construction and manufacturing include adhesives, coatings, sealants and potting compounds, while examples of such material in the medical field include dental impressioning material. Dual chamber dispensing systems often include a replaceable cartridge that has separate, side-by-side barrels with chambers that each hold one component of the material to be dispensed. Examples of dual chamber dispensing cartridges are described in U.S. Pat. Nos. 4,538,920 and 5,236,108.

Many dual chamber dispensing systems also include an applicator having a receptacle for removably receiving a dual chamber cartridge. Some applicators are adapted to be held by the hand during use, and include a pair of handles that, when squeezed together, simultaneously advance a pair of side-by-side plungers by means of a ratchet mechanism. As the plungers advance, the ends of the plungers contact respective pistons located in the chambers of the dispensing cartridge and move the pistons in a forwardly direction toward the front of the cartridge. As the pistons advance, the pistons expel the two components contained in both chambers simultaneously through respective outlets that are located near the front of the cartridge. Examples of hand-held applicators for dual chamber dispensing cartridges are described in EP Publication No. 0 539 074 A1, U.S. Pat. No. 5,137,181 and pending U.S. patent application Ser. No. 08/547,370 entitled "HAND-HELD APPLICATOR WITH FORCE LIMITING CLUTCH"

In some instances, and particularly in construction, manufacturing and industrial applications, electric or pneumatic operated applicators are used to dispense compositions from dual chamber dispensing cartridges. Electric applicators may be battery powered for convenient, hand-held manipulation, or instead may be powered by line current, a particular advantage when relatively large quantities of the components are to be dispensed. In areas where compressed air is readily available, air powered applicators may be preferred. Examples of powered dispensing applicators are described in U.S. Pat. Nos. 5,020,693, 5,064,098 and 5,080,493.

Dual chamber dispensing systems also often include a static mixer for mixing the components that are expelled from the cartridge. The static mixer includes an exit conduit that is detachably coupled to the front end of the cartridge and that communicates with the two spaced apart front outlets of the cartridge. A static mixing element is located within the exit conduit and includes a series of helical shaped mixing sections. When the plungers of the applicator are advanced to expel components from the cartridge, the components pass through the exit conduit where they are thoroughly mixed together by the successive mixing sections and then discharged through a front opening of the exit conduit, optionally directly to an application site. Examples of static mixers are described in U.S. Pat. No. 4,538,920 and PCT publication no. WO 95/22941.

In the dental arena, dual chamber dispensing systems are used to dispense two component impressioning material so that a model of the patient's teeth and gingiva can be obtained. In some procedures, the mixed impressioning material is dispensed into a dental impression tray that is then placed in the patient's oral cavity over selected teeth and gingiva. Once the material hardens, the tray is removed from the mouth and a model of the patient's teeth and gingiva is made by pouring a hardenable plaster of Paris solution, a resin or other molding material into the negative image formed in the impressioning material. After the molding material has hardened, the impressioning material is removed from the molding material in order to obtain a positive model of the patient's teeth and gingiva.

Dispensing cartridges are typically sold containing a larger quantity of impressioning material components than is expected to be needed to fill a typical tray. One reason that the cartridges contain a larger quantity of components than expected to be needed is due to the fact that the trays are available in a wide range of shapes and sizes, so that a particular tray can be selected to match the shape and size of the patient's dental arch that is encountered in practice. Manufacturers typically supply cartridges with a sufficient quantity of components to fill the largest expected tray. Consequently, unless the selected tray is unusually large, a quantity of the components often remains in the cartridge after the tray has been filled.

A dental impressioning dispensing cartridge that has been only partially emptied after a single use is sometimes used in a subsequent dispensing operation to place impressioning material in a second impression tray. However, a previously used cartridge often does not contain a sufficient quantity of the components to fill a second tray, and as a result the dispensing operation must be interrupted once the first cartridge is empty to replace the empty cartridge with a second cartridge. Unfortunately, there is often only a relatively short working time that is available for the practitioner to place and properly position the tray with the impressioning material in the oral cavity once the components are mixed and dispensed into the tray. If the dispensing operation is interrupted to remove an empty cartridge and install a full cartridge in the applicator, such an interruption necessarily reduces the amount of time available for the practitioner to place and properly orient the impression tray in the oral cavity.

As a consequence, many practitioners prefer to start with a new dispensing cartridge in the applicator each time that an impressioning tray is to be filled in order to avoid any reduction in the amount of time available to place and orient the tray in the oral cavity. Partially empty cartridges can be discarded, but such practice represents waste.

Similar problems exist in other fields where dual chamber dispensing cartridges are used. For example, when dispensing a fast-setting epoxy used in a manufacturing process, the user may not have sufficient time to replace an empty cartridge with a full cartridge during a dispensing operation. In such circumstances, the user may opt to start with a new cartridge at the beginning of each procedure, and discard any partially empty cartridges as waste.

Clearly, there exists a need in the art for a device that prevents such waste so that substantially all of the components in a cartridge can be used. Preferably, such a device would not interrupt a dispensing procedure so that the working time of the dispensed material is not reduced.

SUMMARY OF THE INVENTION

One aspect of the present invention relates to a device for consolidating compositions contained in partially filled dual chamber dispensing cartridges. The device includes a body having a pair of side-by-side passages, and a retainer movably connected to the body. The retainer includes a member and a first coupler connected to the member for releasably coupling the body to a first dual chamber dispensing cartridge in an orientation where the passages are in communication with side-by-side outlets of the first cartridge. The retainer also includes a second coupler connected to the member for releasably coupling the body to a second dual chamber dispensing cartridge in an orientation wherein the passages are in communication with side-by-side outlets of the second cartridge. The member is movable relative to the body between a first position wherein the first coupler has coupled the body to the first cartridge and a second position wherein the body may be released from the first cartridge. The device also includes at least one snap-action element associated with at least one of the body and the retainer that releasably retains the member in at least one of the positions.

Another aspect of the present invention is related to a device for consolidating compositions contained in partially filled dual chamber dispensing cartridges, wherein the device includes a body having a pair of side-by-side passages, and a retainer having a hollow member with a first part and a second part. The body is received in the hollow member. The retainer includes a first coupler connected to the first part for releasably coupling the body to a first dual chamber dispensing cartridge in an orientation where the passages are in communication with side-by-side outlets of the first cartridge. The retainer also includes a second coupler connected to the second part for releasably coupling the body to a second dual chamber dispensing cartridge in an orientation wherein the passages are in communication with side-by-side outlets of the second cartridge. The first part and the second part are movable relative to the body, and the first part is movable relative to the second part in order to permit independent coupling of the first coupler and the second coupler to the first cartridge and the second cartridge respectively.

The invention also relates in another aspect to a device for consolidating composition contained in partially filled dual chamber dispensing cartridges, and includes a body having a first section and a second section. Each of the sections includes a pair of side-by-side passages. The body also includes a pair of lengths of flexible tubing that extends between the sections and communicates respective passages. The device also includes a retainer having a hollow member, a first coupler connected to the hollow member and a second coupler connected to the hollow member. The body is received in the retainer, and at least one of the sections is movable relative to the retainer during coupling of the device to a dispensing cartridge.

The device of the invention serves to fill a new, empty cartridge or to refill or partially refill a cartridge that has been previously used. In practice, the device may be used to sequentially connect several partially empty cartridges to a selected host cartridge until the host cartridge is substantially or completely filled with components. The host cartridge can then be used to dispense without interruption a quantity of components that is substantially equal to the quantity of components contained in a new cartridge. The invention serves to greatly reduce waste of the components because substantially all of the components of each cartridge can be beneficially used without adversely affecting the dispensing procedure.

Further aspects and details of the invention are described in the paragraphs that follow and in the accompanying drawings.

BRIEF DESCRIPTION OF THE DRAWINGS

FIG. 1 is a perspective view of a dual chamber dispensing cartridge refilling device according to one embodiment of the invention;

FIG. 2 is a reduced perspective view of the device illustrated in FIG. 1 along with one of two dual chamber dispensing cartridges that may be coupled together by the device;

FIG. 7 is a reduced perspective view of the retainer shown in FIG. 5 and the adapter body shown in FIG. 6 along with a dual chamber dispensing cartridge, depicting the retainer, adapter body and cartridge as they might appear before assembly to one another;

FIG. 8 is a fragmentary, reduced perspective view somewhat similar FIG. 7 except that a second dual chamber dispensing cartridge has been added and the retainer and adapter body have been fully coupled to the front ends of both cartridges;

FIG. 12 is a perspective view of a unitized dual chamber dispensing cartridge refilling device according to still another embodiment of the invention;

FIG. 13 is a front elevational view of the refilling device illustrated in FIG. 12;

FIG. 14 is a reduced perspective view of the refilling device shown in FIGS. 12 and 13 along with a portion of a dual chamber dispensing cartridge, as the device and cartridge might appear before they are coupled together;

FIG. 15 is a fragmentary, reduced perspective view somewhat similar to FIG. 14 except that a second dual chamber dispensing cartridge has been added and the refilling device has been illustrated as coupling the two cartridges together;

FIG. 16 is a perspective view of a dual chamber dispensing cartridge refilling device according to another embodiment of the invention;

FIG. 17 is an end elevational view of the device shown in FIG. 16;

FIG. 18 is a side cross-sectional view of the device shown in FIGS. 16 and 17, taken Along lines 18—18 of FIG. 17;

FIG. 19 is an enlarged perspective view of an adapter body of the device shown in FIGS. 16–18;

DETAILED DESCRIPTION OF THE PREFERRED EMBODIMENTS

Figure 4:
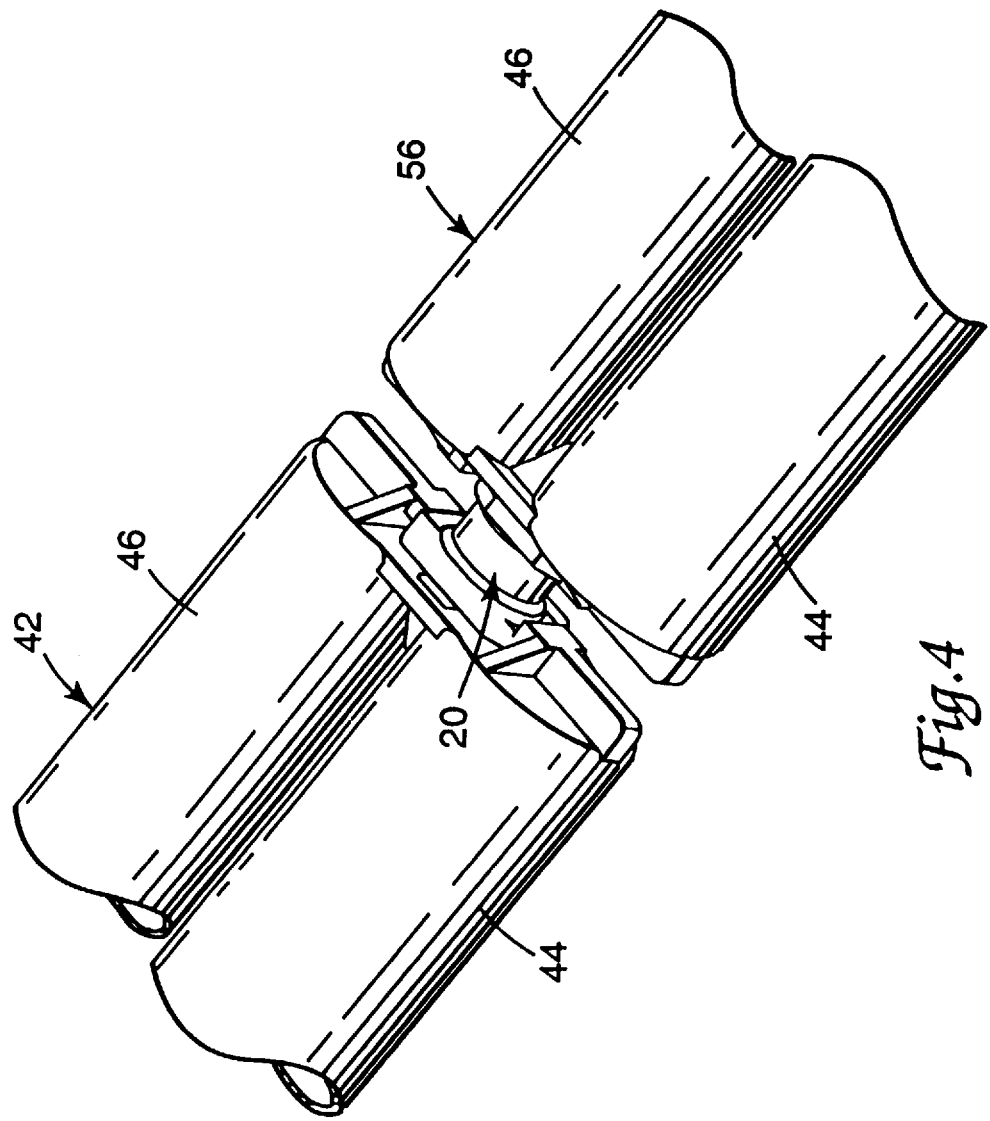
FIG. 4 is a fragmentary, reduced perspective view somewhat similar to FIG. 2 except that a second cartridge has been added and the two cartridges have been coupled to the refilling device.

A device for consolidating compositions contained in partially filled dual chamber dispensing cartridges is designated broadly by the numeral 20 in FIGS. 1, 2 and 4 according to one embodiment of the invention. The device 20 in the particular embodiment shown includes a hollow, cylindrical body 22 that has a first passage 24 and a second passage 26. The passages 24, 26 are separated by a dividing wall 28 that extends across the middle of the interior of the body 22 from one side to another.

The passages 24, 26 are in side-by-side relation to each other and have a generally D-shaped configuration. The dividing wall 28 is recessed on opposite sides from respective ends of the hollow body 22. A chamfered wall section 53 (see FIG. 1) is located on each side of the dividing wall 28 between the dividing wall 28 and respective ends of the body 22.

The device 20 also includes a first coupler 30 that is connected to one end of the body 22 and a second coupler 32 that is connected to an opposite end of the body 22. Each of the couplers 30, 32 includes two opposed, curved flanges 34 having a curved outer edge. The curved flanges 34 of each coupler 30, 32 are integrally interconnected to each other by respective pairs of straight flanges 36 having straight outer edges.

Preferably, and as illustrated for example in FIG. 1, each of the curved flanges 34 has an inclined or ramped surface 38 and a noninclined or "level" surface 43 that face the curved flange 34 of the other coupler 30, 32. In addition, each of the curved flanges 34 includes a stop portion 40 that is located next to the end of the respective level surface 43 and is adjacent a corresponding straight flange 36. When the device 20 is held in a vertical orientation wherein an imaginary central reference axis of the body 22 extends in a vertical direction and when the viewer is looking toward the curved outer edge of the curved flanges 34, the ramped surface 38 of the lowermost curved flange 34 is inclined in an upwardly direction as the right side of such curved flange 34 is approached, and the stop portion 40 is located next to the upper end and to the right of such ramped surface 38.

Preferably, the body 22 and the couplers 30, 32 are integrally molded of a rigid, durable material that does not degrade or react with compositions passing through the passages 24, 26. Suitable materials include synthetic resinous materials such as polyethylene or polypropylene.

The device 20 is adapted for use with a pair of dual chamber dispensing cartridges such as the dispensing cartridge 42 illustrated in FIG. 2. Such cartridges are well known in the art (see, e.g., U.S. Pat. No. 5,236,108) and include a first and second elongated barrel or container 44, 46. The first container 44 has an inner cylindrical chamber (not shown) that is in communication with a first outlet 48 located at the front of the cartridge 42. Similarly, the second container 46 includes an inner cylindrical chamber in communication with a second, front outlet 50. Both of the outlets 48, 50 are contained within a cylindrical, protruding neck or outlet conduit 51 of the front end of the cartridge 42. As shown in FIG. 2, the outlet conduit 51 includes a central baffle that separates the outlets 48, 50 from each other. The outer wall of the outlet conduit 51 includes a front cylindrical surface and a rear chamfered wall section located between the front cylindrical surface and the front end of the containers 44, 46.

The front end of the cartridge 42 also includes a pair of opposed tabs 52 that are located on opposite sides of the outlet conduit 51 and extend toward each other. Each tab 52 is integrally joined to a pair of triangular reinforcing wall sections that extend parallel to the baffle. Each tab 52 is also integrally connected to a rectangular reinforcing wall section that extends perpendicularly to the baffle.

The cartridge 42 also has a rectangular rear flange 54 that is adapted to releasably fit into a cartridge receptacle of an applicator (not shown). The applicator may be hand powered or driven by an electric motor or pneumatic power as described above.

Each chamber of the cartridge 42 is adapted to contain one component or composition of a two component material such as dental impressioning material. Each chamber of the cartridge 42 is provided with a piston (not shown) for engagement with movable plungers of the applicator. As the plungers advance and move the pistons toward the front end of the cartridge 42, components in the chambers are directed through respective outlets 48, 50 in separate, spaced apart streams.

The cartridge 42 may be any one of a number of commercially available cartridges such as the cartridge available with purchase of 3M's silicone dental impressioning material (catalog no. 7302H). Such cartridges are often integrally molded of a synthetic resinous material such as polypropylene; however, other materials such as nylon, polyethylene or acetal may also be employed.

A second cartridge 56 is illustrated in FIG. 4. The second cartridge 56 is identical to the first cartridge 42 and as such a detailed description of the second cartridge 56 need not be provided. In FIG. 4, elements of the second cartridge 56 that are designated by numerals are identical to like-numbered elements of the first cartridge 42.

In use, the device 20 is moved toward the first cartridge 42 along a reference axis 57 while being held in the orientation that is shown in FIG. 2. In that orientation, the straight edges of the straight flanges 36 are parallel with the straight, inwardly facing edges of the tabs 52 of the first cartridge 42. The distance between the straight outer edges of the straight flanges 36 of the first coupler 30 is somewhat less than the distance between the straight inner edges of the tabs 52 such that the flanges 36 move past the tabs 52 at the same time that the protruding outlet conduit 51 surrounding the outlets 48, 50 moves into the interior of the body 22.

Once the circular, outer edge of the cartridge outlet conduit 51 contacts the chamfered wall section 53 of the body 22, the device 20 is rotated by hand relative to the first cartridge 42 in a direction as indicated by the arrow in FIG. 2 about the reference axis 57. The reference axis 57 is collinear with the central axis of the body 22 and is parallel to the longitudinal axes of the containers 44, 46. As the device 20 rotates about the axis 57, the curved flanges 32 pass beneath the overhanging tabs 52, and the ramped surfaces 38 cause the chamfered wall section 53 next to the first coupler 30 to be pressed in snug, sealing engagement with the outer edge of the outlet conduit 51. The device 20 is further rotated about the axis 57 in such fashion as the level surfaces 43 slide beneath the tabs 52 until the stop portions 40 of the first coupler 30 engage the sides of the tabs 52 and prevent further rotation.

The dividing wall 28 of the device 20 is aligned in coplanar fashion with the outlet baffle of the first cartridge 42 when the device 20 is fully installed on the first cartridge 42 such that the stop portions 40 of the first coupler 30 are in contact with the tabs 52. The outer edge of the dividing wall 28 facing the first cartridge 42 is spaced inwardly from the adjacent outer edge of the device 20 a distance to enable the device 20 to be fully seated on the protruding outlet conduit 51, and yet also enable the adjacent outer edge of the dividing wall 28 to be in firm, leak-resistant contact with the front edge of the baffle between the outlets 48, 50.

Next, the second cartridge 56 is moved toward the device 20 while being held in such an orientation that the straight, facing wall sections of the tabs 52 of the second cartridge 56 are parallel with the straight outer edges of the straight flanges 36 of the second coupler 32. The outlet conduit 51 of the second cartridge 56 is then moved into the interior of the body 22 until the interior, chamfered wall section 53 next to the second coupler 32 contacts the outer circular edge of the protruding outlet conduit 51 of the second cartridge 56.

Subsequently, the second cartridge 56 is turned about the axis 57 in the direction indicated by the arrow in FIG. 2 relative to the first cartridge 42 such that the curved flanges 34 of the second coupler 32 move beneath the tabs 52 of the second cartridge 56 in a manner identical to the locking, coupling movement of the first coupler 30 as described above when the device 20 is connected to the first cartridge 42. When the second cartridge 56 is fully and securely coupled to the device 20, the second cartridge 56 is aligned with the first cartridge 42 in the manner shown in FIG. 4 wherein the central, longitudinal axes of the first containers 44 are collinear relative to each other and the central, longitudinal axes of the second containers 46 are collinear relative to each other. Furthermore, when the cartridges 42, 56 are both fully coupled to the device 20, the first outlets 48 of the cartridges 42, 56 are in communication only with the first passage 24 and the second outlets 50 of the cartridges 42, 56 are in communication only with the second passage 26.

Next, an applicator is connected to one of the cartridges 42, 56, depending on which cartridge is designated as the host cartridge. If, for example, the first cartridge 42 is selected as the host cartridge to be refilled, the applicator is connected to the second cartridge 56. Typically, although not necessarily, the applicator has a receptacle as mentioned above to receive the rear cartridge flange 54 of the second cartridge 56. The applicator also includes plungers or the like to advance the cartridge pistons.

Figure 3:
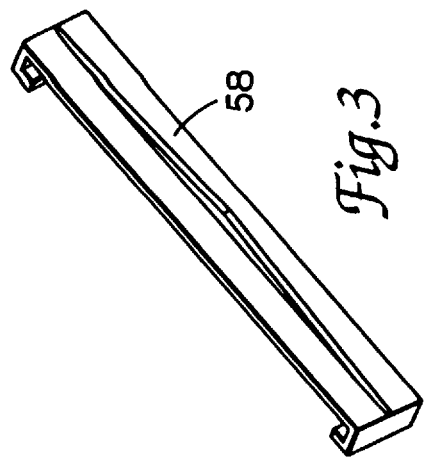
FIG. 3 is a perspective view of a retaining clip alone that is also illustrated in FIG. 2.

Preferably, a stop clip 58 (FIGS. 2 and 3) is placed over the rear flange 54 of the first cartridge 42 before the plungers of the applicator are advanced to move the pistons of the second cartridge 56. The stop clip 58 has a pair of opposed "U"-shaped end sections that complementally engage opposite sides of the rear flange 54. The stop clip 58 prevents the pistons of the first cartridge 42 from moving past the open, rear ends of the containers 44, 46 and detaching from the cartridge 42 while the components are introduced into the first cartridge 42. The stop clip 58 is preferably made of a resilient material such as injection-molded plastic or spring steel that can be readily attached and detached from the rear flange 54 as needed.

The applicator is then operated to advance the plungers and move the pistons of the second cartridge 56 forwardly and toward the first cartridge 42. As the pistons so move, the components within the second cartridge 56 are expelled through the outlets 48, 50 of the second cartridge 56, through the passages 24, 26 of the body 22 and then through respective outlets 48, 50 of the first cartridge 42 and into the containers 44, 46 of the first cartridge 42. Preferably, the plungers of the applicator are advanced sufficiently to direct essentially all of the components remaining in the second cartridge 56 through the device 20 and into the first cartridge 42.

As the components pass from the second cartridge 56 into the first cartridge 42, the passages 24, 26 function to keep the components separated so that cross-contamination and possible reaction of the components cannot occur. The size and configuration of the dividing wall 28, the baffle, the outer edge of the outlet conduit 51 and the chamfered wall section 53 provide sealing contact between the body 22 and the cartridges 42, 56 when coupled together in the manner shown in FIG. 4 so that cross-contamination of the components or leakage of the components to areas external of the device 20 is essentially prevented.

Once the components in the second cartridge 56 have been emptied into the first cartridge 42 (or, alternatively, once the pistons of the first cartridge 42 have come into contact with the stop clip 58), advancement of the plungers of the applicator is interrupted. If, for example, the second cartridge 56 is now empty, the second cartridge 56 is removed from the applicator. The second cartridge is also detached from the device 20 by turning the second cartridge 56 in a direction opposite to the arrow in FIG. 2 relative to the first cartridge 42 until the straight outer edges of the straight flanges 36 are aligned with the straight, facing edges of the tabs 52 of the second cartridge 56. The second cartridge 56 is then moved away from the device 20 along axis 57 (FIG. 2). The above procedure is then repeated with another partially filled cartridge in place of the second cartridge 56.

On the other hand, if the first cartridge 42 is filled before the components have been completely expelled from the second cartridge 56, the first cartridge 42 is detached from the device 20 by rotating the first cartridge 42 relative to the device 20 and the second cartridge 56 in a direction opposite to that of the arrow shown in FIG. 2. The first cartridge 42 is then uncoupled from the device 20 and another cartridge that is empty or partially empty is reinstalled in its place.

Although not shown, an alignment or orienting section may optionally be provided to insure that the device 20 cannot be connected to the first cartridge 42 or the second cartridge 56 unless each first container 44 is ultimately in alignment with the first passage 24 and each second container 56 is ultimately in alignment with the second passage 26. The orienting section may take any of several forms. One possible orienting section could be constructed by providing the curved flanges 34 of each coupler 30, 32 with different lengths in directions radially of the central axis of the body 22, and also providing cartridges with tabs 52 that are matingly offset corresponding distances from the outlet conduit 51. In such structure, the tabs 52 prevent coupling of the cartridges 42, 56 to the device 20 unless the containers 44, 46 of one cartridge have been oriented for ultimate proper alignment with the containers 44, 46 of the other cartridge as well as with the passages 24, 26 of the body 22.

A dual chamber dispensing cartridge refilling device 20*a* according to a second embodiment of the invention is illustrated in FIGS. 5–8. The device 20*a* includes a retainer 21*a* that is shown alone in FIG. 5 and an adapter body 22*a* that is shown alone in FIG. 6.

The retainer 21*a* includes a central member 23*a* that is hollow and cylindrical, and lacks a central dividing wall (such as dividing wall 28 described above). A first coupler 30*a* and a second coupler 32*a* are integrally connected to opposite ends of the member 23*a*. Each of the couplers 30*a*, 32*a* includes two curved flanges and two straight flanges that are identical to the flanges 34, 36 respectively described above. Preferably, but not necessarily, each curved flange includes a ramped surface, a level surface and a stop portion that are identical to the ramped surface 38, the level surface 43 and the stop portion 40 respectively.

Figure 5:
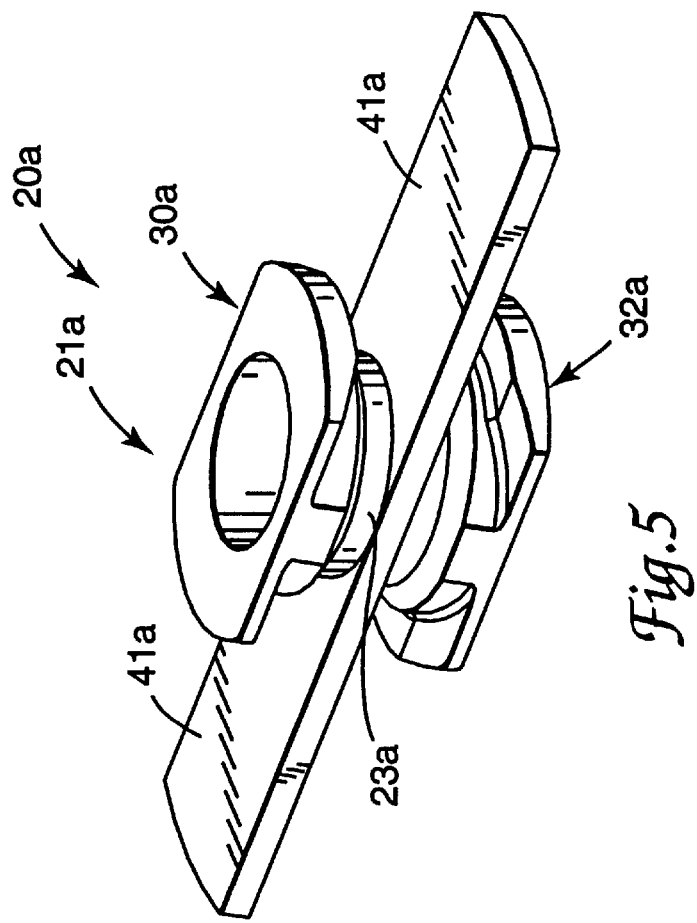
FIG. 5 is a perspective view of a retainer that is part of a dual chamber dispensing cartridge refilling device according to another embodiment of the invention.

The retainer 21*a* also includes a pair of arms 41*a* that are connected to the member 23*a* and extend outwardly away from each other in opposite directions. As depicted in FIG. 5, the arms 41*a* extend in a direction that is parallel to the straight outer edges of the straight flanges, although other directions are also possible. Moreover, while two arms 41*a* are shown, the retainer 21 a could alternatively have a greater number or a smaller number of such arms.

Figure 6:
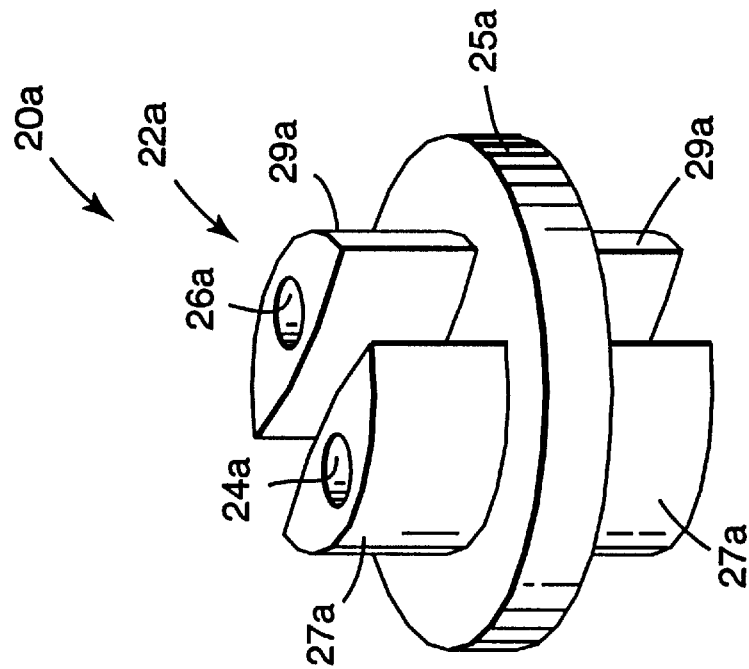
FIG. 6 is an enlarged perspective view of an adapter body that is also part of the refilling device described in connection with the retainer shown in FIG. 5.

Referring now to FIG. 6, the adapter body 22*a* includes a central, circular plate 25*a* and two pairs of projections 27*a*, 29*a*. The projections 27*a* are aligned with each other, and a first passage 24*a* extends through the projections 27*a* as well as through the plate 25*a*. Similarly, the projections 29*a* are aligned with each other and a second passage 26*a* extends through the two projections 29*a* as well as through the plate 25*a*.

In use, the body 22*a* is aligned with the first cartridge 42 in the manner shown in FIG. 7 such that the projections 27*a*, 29*a* on one side of the plate 25*a* are aligned with the first outlet 48 and the second outlet 50 respectively. The body 22*a* is then moved toward the first cartridge 42 and along reference axis 57*a* such that the projections 27*a*, 29*a* on the side of the plate 25*a* facing the first cartridge 42 enter the outlets 48, 50 respectively. When the projections 27*a*, 29*a* are fully inserted into the outlets 48, 50 of first cartridge 42, the facing wall section of the plate 25*a* flatly contacts the outer edge of the outlet conduit 51 including the outer edge of the baffle.

Next, the retainer 21*a* is also moved toward the first cartridge 42 along axis 57*a* while held in the orientation shown in FIG. 7. In such an orientation, the straight flanges are parallel to the facing edges of the tabs 52 in a manner similar to that described above in connection with assembly of the embodiment shown in FIGS. 1, 2 and 4. As the retainer 21*a* moves closer to the cartridge 42, the central member 23*a* moves to a position surrounding the body 22*a*.

Next, the second cartridge 56 is moved toward the body 22*a* while being held in an orientation wherein the longitudinal axes of the containers 44, 46 of the first cartridge are collinear with the longitudinal axes of the containers 44, 46 respectively of the second cartridge. The second cartridge 56 is moved toward the body 22*a* until the projections 27*a*, 29*a* facing the second cartridge 56 are fully inserted into the outlets 48, 50 of the second cartridge 56 and the facing wall section of the plate 25*a* flatly contacts the outer edge of the outlet conduit 51 (including the outer edge of the baffle) of the second cartridge 56.

The retainer 21*a* is then turned by grasping the arms 41*a* and rotating the retainer 21*a* relative to the first cartridge 42 and the second cartridge 56 about the axis 57*a*. The axis 57*a* is collinear with a central axis of the retainer 21*a* and the body 22*a*, and is parallel to the central, longitudinal axes of the containers 44, 46 of both cartridges 42, 56 when connected to the body 22*a*. The first coupler 30*a* operates in a manner identical to that described above in connection with the embodiment shown in FIGS. 1, 2 and 4. Once the arms 41*a* are turned 90 degrees and extend in the direction that is shown in FIG. 8, the retainer 21*a* is securely coupled to the containers 42, 56.

Subsequently, an applicator is connected to one of the cartridges 42, 56 in order to expel components remaining in such cartridge to the other cartridge in a fashion similar to that described above in connection with the embodiment shown in FIGS. 1, 2 and 4. Additionally, a stop clip such as the stop clip 58 shown in FIGS. 2–3 may be provided to prevent undue rearward movement of the pistons of the host cartridge. Once the refilling operation has been completed, the applicator is removed and the cartridges 42, 56 are uncoupled from each other as well as from the refilling device 20*a* by reversing the steps set out above.

Preferably, retainer 21*a* including the cylindrical member 23*a*, the couplers 30*a*, 32*a* and the arms 41*a* are integral and made of a relatively rigid material that does not react with components in the cartridges 42, 56. Suitable materials include metals such as type AISI 302 stainless steel, and plastics such as polysulfone, available from Amoco under the trademark "UDEL".

The body 22*a* is preferably integrally molded of an elastomeric material that does not react with the components in the cartridges 42, 56. Preferably, the elastomeric material does not contain any sulfur compounds that might otherwise hinder the effectiveness of catalysts used in dental impressioning material. Suitable elastomerics include polyurethane and silicone rubbers.

The adapter body 22*a* is preferably resilient and has a relatively low modulus of elasticity so that the body 22*a* readily provides a leak-resistant seal between the device 20*a* and the cartridges 42, 56. The wall sections of the plate 25*a* that are in flat contact with the outer circular edge of the outlet conduit 51 as well as with the outer edge of the baffle function as sealing sections for preventing escape of the components during passage from one cartridge to the other. The thickness of the plate 25*a* is selected to ensure that the plate 25*a* is slightly compressed between the outlet conduits 51 of the cartridges 42, 56 when the cartridges 42, 56 are coupled together by the device 20*a* in the manner depicted in FIG. 8.

Preferably, the retainer 21*a* includes an inner circular shoulder that blocks passage of the body 22*a* completely through the member 23*a*, and instead allows the body 22*a* to be removed through only one of the two open ends of the member 23*a*. The shoulder is an advantage when the body 22a is between the shoulder and the host cartridge, because the body 22a will stay connected to the host cartridge when the other cartridge is detached so long as the retainer 21a also remains connected to the host cartridge.

Optionally, the device 20a includes means for retaining the body 22a in the retainer 21a to facilitate handling and assembly and to prevent the body 22a from becoming misplaced. Such means could comprise, for example, a pair of spaced apart annular retaining rings provided in the interior of the member 23a instead of the shoulder mentioned above, with the plate 25a received in the space between the rings. Such means, however, should enable rotation of the body 22a relative to the retainer 21a as the retainer 21a is turned relative to the cartridges 42, 56, so that the projections 27a, 29a are not damaged and remain in place in the outlets 48, 50 of any cartridge coupled to the retainer 21a.

Figure 9:
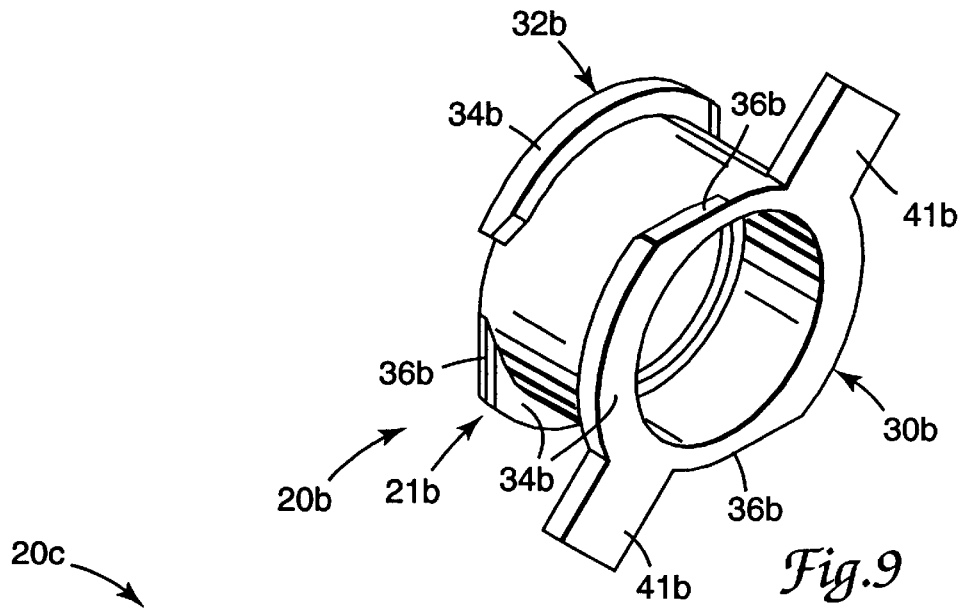
FIG. 9 is a perspective view of a retainer of a dual chamber dispensing cartridge refilling device according to another embodiment of the invention.

An alternative retainer 21b is illustrated in FIG. 9 according to another embodiment of the invention. The retainer 21b is similar to the retainer 21a with the exception of the features noted below.

More particularly, the retainer 21b has a first coupler 30b and a second coupler 32b that is oriented in a somewhat different rotative position relative to the first coupler 30b with reference to a central axis passing through the hollow interior of the retainer 21b. Any one of a number of different rotative orientations can be provided. In the embodiment shown in FIG. 9, the second coupler 32b is oriented approximately 90 degrees about its central axis relative to the first coupler 30b, such that straight outer edges of straight flanges 36b of the first coupler 30b extend in a direction perpendicular to the straight outer edges of straight flanges 36b of the second coupler 32b.

The couplers 30b, 32b include curved flanges that each have a small ramped surface on each end for engagement with the tabs 52, but the couplers lack stop portions similar to the stop portions 40 described above. As such, the retainer 21b may be detached from the cartridges 42, 56 by rotation of the retainer 21b in either direction about its central axis. As an alternative, however, the curved flanges of the couplers 30b, 32b may include larger ramped surfaces and also include stop portions identical to the ramped surfaces 38 and the stop portions 40 described above.

The retainer 21b also has a pair of arms 41b that are connected to flanges 34b, 36b of the first coupler 30b. The arms 41b extend away from each other and at a non-zero angle relative to the straight outer edges of straight flanges 36b of the couplers 30b, 32b. In the embodiment shown, the arms 41b extend at an angle of approximately 45 degrees relative to the straight outer edges of the straight flanges 36b of both the couplers 30b, 32b, although other orientations are, of course, possible.

Figure 10:
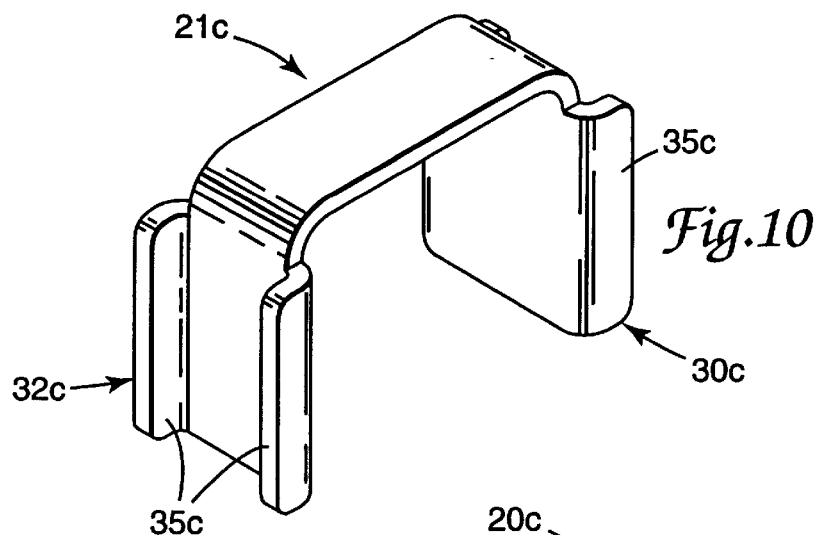
FIG. 10 is a perspective view of a retainer of a dual chamber dispensing cartridge refilling device according to yet another embodiment of the invention.
Figure 11:
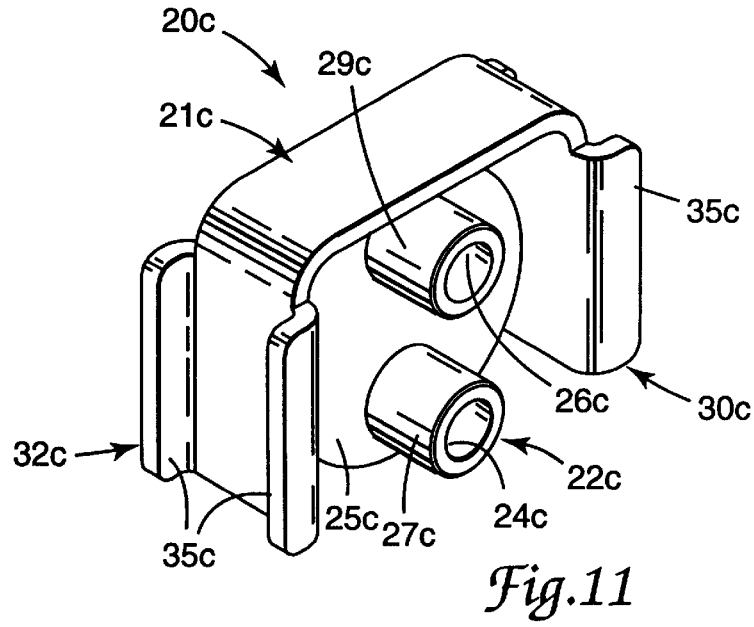
FIG. 11 is a perspective view of the retainer shown in FIG. 10 along with an adapter body that is somewhat different than the adapter body shown in FIG. 6;.

The embodiment of the invention that is illustrated in FIGS. 10 and 11 concerns a dual chamber dispensing cartridge refilling device 20c that includes a retainer 21c that is shown in FIG. 10 alone as well as an adapter body 22c that is shown only in FIG. 11. The retainer 21c is in the form of a clip having an overall "U"-shaped configuration.

The retainer 21c includes a first coupler 30c having a pair of flanges 35c that extend away from each other. The retainer 21c also includes a second coupler 32c having a pair of identical flanges 35c that also extend away from each other. The retainer 21c is preferably integrally made of a stamped section of sheet metal, although alternatively other materials such as the materials described above in connection with the retainer 21a could be used.

The body 22c is somewhat similar to the body 22a, in that the body 22c has a first elongated passage 24c, a second elongated passage 26c and a plate 25c. The body 22c also has projections 27c, 29c surrounding the passages 24c, 26c on one side of the plate 25c. Although not shown, a similar set of projections is provided on the opposite side of the plate 25c. For exemplary purposes, the projections 27c, 29c have an external cylindrical shape, although it should be understood in this regard that the projections could also have other shapes such as a generally "D"-shaped external configuration similar to the shape of the projections 27a, 29a illustrated in FIG. 6.

The projections 27c, 29c are of a certain shape and are spaced apart a distance to match the shape and spacing of outlets of other types of dual chamber dispensing cartridges. For example, the projections 27c, 29c of the body 22c may have a shape matching the outlet ports of the dispensing cartridge illustrated in U.S. Pat. No. 5,333,670. Of course, many other shapes, sizes and spacings are also possible.

In use of the embodiment illustrated in FIGS. 10 and 11, the projections 27c, 29c of the body 22c are placed in the outlets of two dispensing cartridges that face each other. While the cartridges and the body 22c are held in such an orientation, the retainer 21c is moved in a direction that is perpendicular to the longitudinal axes of the passages 24c, 26c. While the retainer 21c is moving in such a direction, the flanges 35c pass beneath tabs (such as tabs 52) of the cartridges in order to couple the device 20c to the two cartridges.

The body 22c is preferably made of an elastomeric material similar to the materials described above in connection with the body 22a. The body 22c provides a seal between the outlet conduits of the dispensing cartridges once the retainer 21c has been installed in place. After the components in one cartridge have been transferred to the other cartridge, the device 20c is uncoupled from the cartridges by moving the retainer 21c away from the body 22c in a direction that is also perpendicular to the longitudinal axes of the passages 24c, 26c until the flanges 30c are released from the tabs of the cartridges.

FIGS. 12–15 illustrate a dual chamber dispensing cartridge refilling device 20d that is constructed according to another embodiment of the invention. The device 20d is shown alone in FIGS. 12 and 13 and includes a body 22d having an elongated, generally cylindrical shape with two spaced apart plates 25d. A pair of projections 27d, 29d extends outwardly from one plate 25d, and a similar pair of projections 27d, 29d extends outwardly from the other plate 25d. The projections 27d, 29d are essentially identical to the projections 27a, 29a described above in that they are each adapted to fit within the confines of spaced apart outlets of a protruding outlet conduit of a dual chamber dispensing cartridge such as cartridges 42, 56. A pair of spaced apart, non-communicating, generally "D"-shaped passages 24d, 26d (FIG. 12) extends through the projections 27d, 29d respectively as well as through the interior of the body 22d.

A first coupler 30d of the device 20d includes a pair of "L"-shaped legs 31d that are integrally connected to one of the plates 25d and extend past the other plate 25d. A second coupler 32d of the device 20d has a similar pair of legs 33d that are integrally connected to the opposite plate 25d and extend toward the plate 25d that is integrally connected to the legs 31d. A triangular brace 37d integrally connects the body 22d and a first, adjacent portion of the legs 31d, 33d that extends outwardly in a radial direction from the body 22d.

Each of the legs 31d, 33d includes an outermost hook 39d that is adapted to fit behind tabs of a dual chamber dispensing cartridge such as tabs 52 of the cartridges 42, 56. A second portion of the legs 31d, 33d extends between the hooks 39d and the first portion. The second portion of the legs 31d, 33d, being not directly connected to the braces 37d, is flexible and can be readily shifted inwardly by finger pressure or otherwise toward the body 22d when desired. Each hook 39d includes an outer chamfered wall for engagement with the tabs of the dispensing cartridges.

In use, the device 20d is oriented relative to the dispensing cartridge 42 in the manner shown in FIG. 14 such that the projections 27d are aligned with the outlets 48, 50. As the device 20d is moved toward the cartridge 42 along reference axis 57d, the chamfered walls of the adjacent hooks 39d contact the tabs 52 and cause the legs 31d to deflect inwardly toward the body 22d until such time as the hooks 39d have moved past the tabs 52. As soon as the hooks 39d of the legs 31d have entered the space between the tabs 52 and the front end of the containers 44, 46 of the cartridge 42, the resilient legs 31d self-move in a direction away from the body 22d and return toward their normal configuration as is illustrated in FIG. 15. Preferably, the applicator is coupled to the cartridge 42 at this time and the plungers of the applicator are advanced to bleed air from the passages 24d, 26d. Next, a second cartridge 56 is connected to the device 20d by moving the second cartridge 56 in a similar manner until such time as the hooks 39d of the legs 33d have latched behind the tabs 52 of the second cartridge 56.

Preferably, the device 20d is integrally molded of a resilient material such as polypropylene. The distance between the hooks 39d of either coupler 30d, 32d and the adjacent plate 25d is selected so that such plate 25d is snugly compressed in flat, sealing engagement against the outer wall of the protruding outlet conduit 51 including the baffle. After the components have been transferred from one cartridge to the other, the device 20d is released from the cartridges 42, 56 by pressing the legs 31d, 33d inwardly toward the body 22d until the hooks 39d have cleared the tabs 52 and then moving the device 20d away from the cartridges 42, 56 along axis 57d.

Preferably, the device 20d includes one or more orienting sections for orienting the device 20d to the cartridges 42, 56 to insure that only the first containers 44 are connected with the first passage 24d and only the second containers 46 are connected to the passage 26d. Although not shown, such orienting sections could be provided by making the shape of the first outlets 48 different than the shape of the second outlets 50, and by providing projections 27d that matingly fit only into the first outlets 48 or projections 29d that matingly fit only into the second outlet 50. Other orienting sections such as outwardly protruding orienting sections like the ones described in U.S. Pat. No. 4,974,756 may alternatively be employed.

If desired, a separate, soft, elastomeric gasket may be provided adjacent each plate 25d surrounding the projections 27d, 29d. The gasket facilitates sealing of the device 20d to the cartridges 42, 56 and enables the body 22d to be made of a stiffer material to improve its strength.

Optionally, the pistons of the cartridges 42, 56 are modified to reduce the likelihood of turning the pistons over as a selected host cartridge is refilled. Such modification may include lengthening of the pistons, or adding spaced apart legs to the piston to hinder such turning motion as may be desired in cartridges where the pistons have a disk-like shape of relatively small thickness.

A dual chamber dispensing cartridge refilling device 20e according to another embodiment of the invention is illustrated in FIGS. 16–18 and 22. The device 20e includes a retainer 21e and an adapter body 22e, the latter of which is shown alone in FIG. 19.

The adapter body 22e includes a central, circular plate 25e and two pairs of projections 27e, 29e. The projections 27e are aligned with each other, and a first passage 24e extends through the projections 27e as well as through the plate 25e. In a similar manner, the projections 29e are aligned with each other and a second passage 26e extends through the two projections 29e as well as through the plate 25e.

The adapter body 22e also includes a pair of resilient elements 60e that are joined to one side of the plate 25e in symmetrical fashion and on opposite sides of the projections 27e, 29e, such that a reference plane that contains a central, longitudinal axis of each element 60e is perpendicular to a reference plane that contains a central, longitudinal axis of each of the passages 24e, 26e. Each of the elements 60e includes an outermost, disk-shaped head and an intermediate section in the shape of a partial cylinder that interconnects the head and the plate 25e. The plate 25e also includes two notches 61e that are adjacent respective locations where the intermediate sections of the elements 60e are connected to the plate 25e.

The retainer 21e includes a hollow, generally cylindrical central member 23e having a groove 62e (FIG. 18) that extends in a circular path completely around an interior wall of the member 23e. The adapter body 22e is received in the hollow interior of the member 23e in a position wherein the peripheral edge of the circular plate 25e is captured in the groove 62e. The plate 25e is slidable in the groove 62e such that the adapter body 22e is pivotally movable in an arc relative to the retainer 21e about a central reference axis that extends through the hollow interior of the member 23e.

The retainer 21e also includes four elongated recesses 63e that are partially shown in FIG. 16 and 18. The recesses 63e extend from the groove 62e to one end of the hollow member 23e and are spaced apart from each other at ninety degree intervals around the interior wall of the member 23e. As the adapter body 22e is rotated relative to the retainer 21e, the heads of the elements 60e snap into a respective pair of the recesses 63e as the latter approach the elements 60e. Further rotative movement of the adapter body 22e relative to the retainer 21e causes the elements 60e to deflect inwardly toward each other such that the disk-shaped heads move out of the recesses 63e and remain in such a deflected orientation until reaching the next respective pair of recesses 63e.

The retainer 21e includes a first coupler 30e and a second coupler 32e (FIG. 18) that are fixedly joined to opposite, respective end sections of the hollow member 23e. The first coupler 30e includes a pair of curved flanges 34e as well as a projection 66e having a triangular shape. As shown for example in FIG. 17, the flanges 34e are arranged such that the space between opposed ends of the flanges 34e in the vicinity of the projection 66e is larger than the space between the remaining ends of the flanges 34e, and as a result a non-symmetrical relationship of one flange 34e to the other is presented.

The second coupler 32e is identical (in mirror image) to the first coupler 30e, and as a consequence a detailed description of the second coupler 32e need not be provided. Between the first coupler 30e and the second coupler 32e, a pair of spaced apart annular arms or disks 41e are provided and are fixed to the hollow member 23e. Each of the flanges 34e of the first coupler 30e and the second coupler 32e are connected near one end to a transverse, bar-like rectangular stop 68e (see, e.g., FIG. 16) that extends toward the adjacent annular disk 41e.

Figure 20:
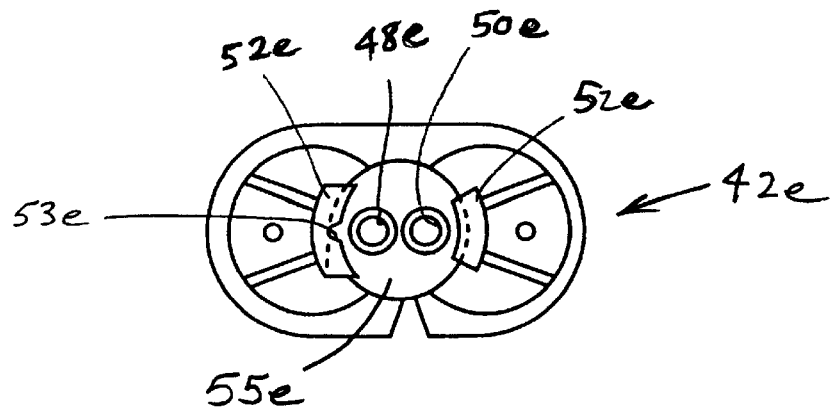
FIG. 20 is a reduced end elevational view of a dual chamber dispensing cartridge that is especially suitable for use with the refiling device shown in FIGS. 16–18.
Figure 21:
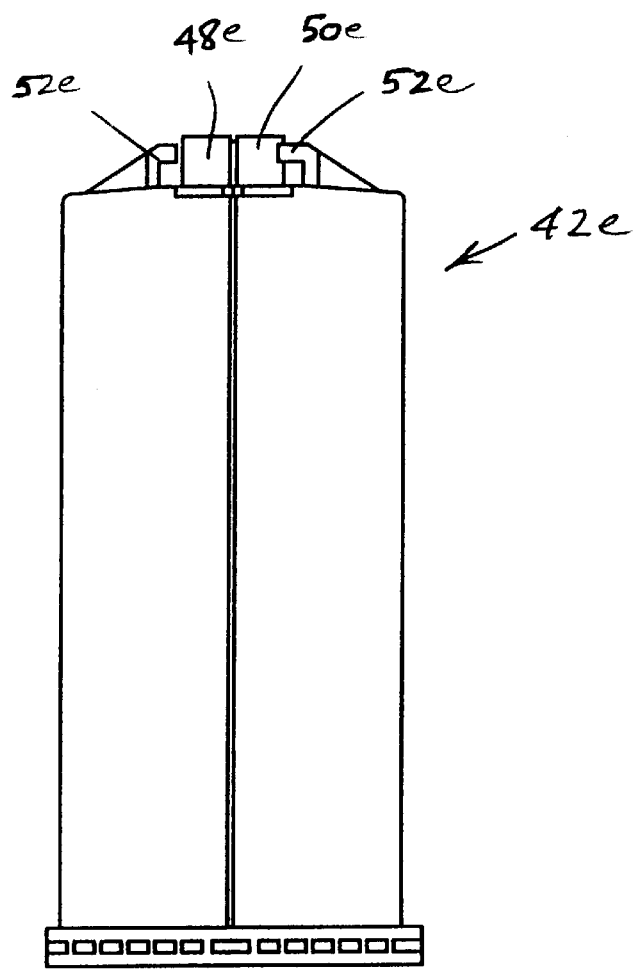
FIG. 21 is a side elevational view of the dispensing cartridge depicted in FIG. 20.

The refilling device 20e is especially adapted for use with a pair of dual chamber dispensing cartridges such as the dispensing cartridge 42e illustrated in FIGS. 20 and 21. The cartridge 42e is somewhat similar to the dispensing cartridge 42 illustrated in FIG. 2, in that it includes a first and second elongated barrel or container each having an inner cylindrical chamber, and each chamber is adapted to contain one component or composition of a two component material such as dental impressioning material. Each chamber of the cartridge 42e is provided with a piston (not shown) for engagement with movable plungers of an applicator. As the plungers advance and move the pistons toward the front end of the cartridge 42e, components in the chambers are directed through respective cylindrical, tubular outlets 48e, 50e in separate, spaced apart streams.

As depicted in FIGS. 20 and 21, the front end of the cartridge 42e includes a pair of opposed, curved tabs 52e that are located on opposite sides of the outlets 48e, 50e. One of the tabs 52e is shorter in length and corresponds in size to the smaller of the two spacings between opposed ends of the curved flanges 34e of either coupler of the retainer 21e as shown in FIG. 17. The other tab 52e is somewhat longer in length and corresponds in size to the distance between the remaining ends of the flanges 34e shown in FIG. 17. The longer curved tab 52e also includes a triangular-shaped notch 53e (FIG. 20) that matches the configuration and orientation of the projection 66e of either coupler of the retainer 21e.

Figure 22:
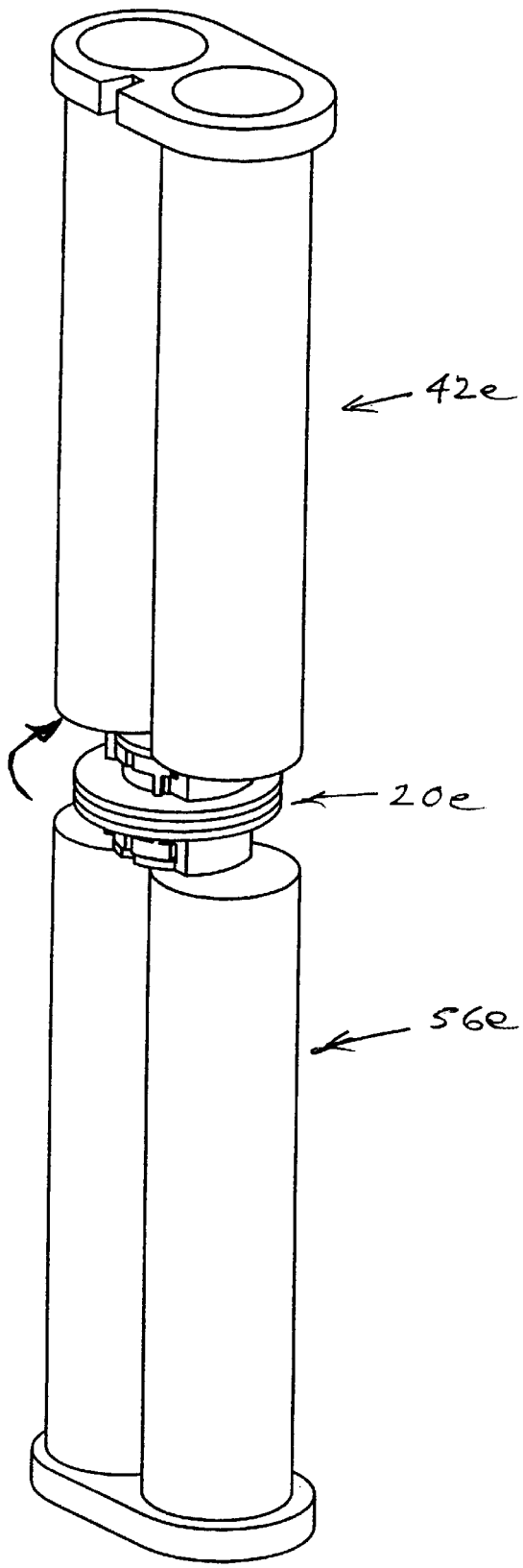
FIG. 22 is a reduced perspective view showing two cartridges of the type illustrated in FIGS. 20–21 that are coupled together by the refilling device illustrated in FIGS. 16–18.

A second cartridge 56e is illustrated in FIG. 22. The second cartridge 56e is identical to the first cartridge 42e and as such a detailed description of the second cartridge 56e need not be provided.

In use, the device 20e is moved toward the first cartridge 42e along its central reference axis while being held in an orientation such that the curved tabs 52e are aligned with the appropriate, matching spaces between the curved flanges 34e respectively. Movement of the cartridge 42e toward the refilling device 20e is continued until such time as an outer, annular end wall of the hollow member 23e and adjacent wall sections of the curved flanges 34e flatly contact a circular wall 55e (see FIG. 20) of the cartridge 42e. When such contact has occurred, the outlets 48e, 50e surround the adjacent pair of projections 27e, 29e in sealed relation. Optionally, outer walls of the projections 27e, 29e and/or inner walls of the outlets 48e, 50e may be slightly tapered or have a chamfered entrance in order to facilitate connecting the device 20e to the cartridge 42e and yet provide sealing sections that reduce the risk of leakage during a subsequent refilling operation.

Next, the second cartridge 56e is moved toward the device 20e while being held in such an orientation that the curved tabs 52e and the notch 53e are aligned with the curved flanges 34e and the projection 66e respectively. Movement of the second cartridge 56e toward the device 20e is continued in the manner described above with respect to the first cartridge 42e until such time as a circular wall (identical to wall 55e) of the second cartridge 56e contacts the adjacent annular end of the hollow member 23e and adjacent wall sections of the curved flanges 43e.

Subsequently, the disks 41e are gripped to turn the retainer 21e about its central axis in a direction indicated by the arrow in FIG. 22 while the cartridges 42e, 56e are held in a stationary position. Such turning motion of the retainer 21e continues until the stops 68e of each coupler 30e, 32e contact adjacent, respective ends of the curved tabs 52e. At such time, the flanges 34e are disposed between the tabs 52e and the circular wall 55e of each of the cartridges 42e, 56e in order to releasably lock the refilling device 20e to the cartridges 42e, 56e.

As the retainer 21e is turned relative to the cartridges 42e, 56e, the adapter body 22e remains stationary and does not move relative to the cartridges 42e, 56e, inasmuch as the projections 27e, 29e are received and locked into place in the outlets 48e, 50e of each cartridge 42e, 56e. As the retainer 21e is turned, the groove 62e of the central hollow member 23e slides along the outer, circular edge of the adapter body 22e. Optionally, leading edges of the curved flanges 34e and/or of the curved tabs 52e may be tapered or chamfered in order to facilitate locking the refilling device 20e to the cartridges 42e, 56e and ensure that the outlets 48e, 50e are snugly and sealingly engaged with the projections 27e, 29e.

Next, an applicator is connected to one of the cartridges 42e, 56e and a stop clip (such as the stop clip 58 in FIGS. 2 and 3) is placed over the rear flange of the outer cartridge 42e, 56e. The applicator is operated in the manner described above with reference to the embodiment shown in FIGS. 1–4 in order to expel the components within the chambers of the cartridge connected to the applicator through the respective passages 24e, 26e and into the chambers of the remaining cartridge. As can be appreciated, the triangular projections 66e of the device 20e, in cooperation with the mating notches 53e of the cartridges 42e, 56e provide consistent orientation of the cartridges 42e, 56e to each other and to the refilling device 20e so that the composition in the first chamber of the cartridge 42e cannot be directed to the second chamber of the second cartridge 56e and the composition in the second chamber of the first cartridge 42e cannot be directed to the first chamber of the second cartridge 56e. As a consequence, the compositions are not inadvertently intermixed.

The elements 60e releasably hold the adapter body 22e in a selected rotative position relative to the retainer 21e. For example, the elements 60e are able to releasably hold the body 22e in the orientation shown in FIGS. 16 and 17 regardless of vibration or jostling of the device 20e that may occur during shipping of the device 20e to the user. As a result, the device 20e remains in a ready-to-use configuration for quick connection to a cartridge when desired.

Moreover, as the retainer 21e is rotated relative to the cartridges 42e, 56e, the elements 60e provide tactile feedback to the user that the intended rotative position of the retainer 21e has been reached. For example, when the retainer 21e is turned in a direction opposite to the direction of the arrow shown in FIG. 22e to uncouple the device 20e from the cartridges 42e, 56e, the elements 60e snap into respective recesses 63e once the projections 66e are aligned with the notches 53e and the curved flanges 34e are aligned with the spaces between the tabs 52e. The snap-action movement of the elements 60e provides a signal to the user that the device 20e can now be removed from the cartridges 42e, 56e.

Perferably, the retainer 21e and the body 22e are each integrally molded of a synthetic resinous material Suitable plastics for the retainer 21e include, for example, polypropylenes and polyethylenes. Suitable plastics for the body 22e include, for example, acetals such as DELRIN brand material from DuPont.

Figure 23:
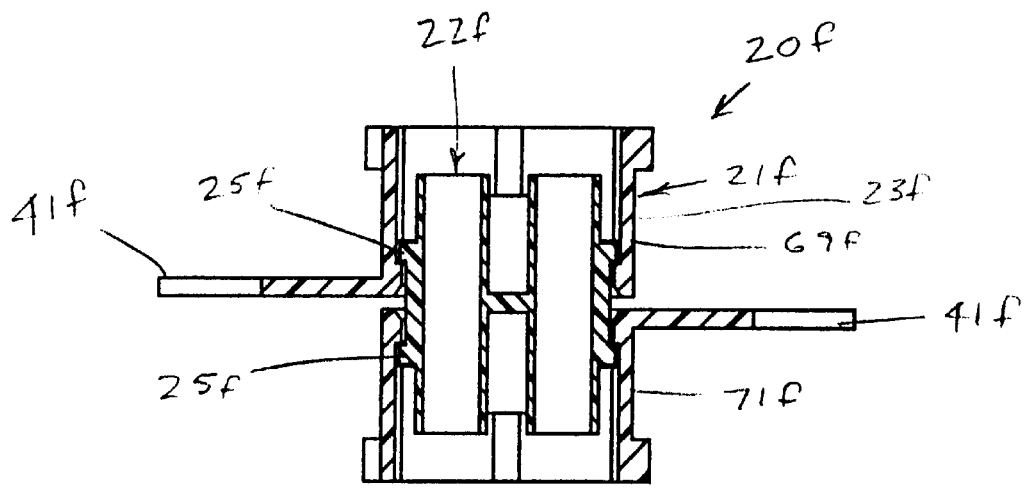
FIG. 23 is a side cross-sectional view of a dual chamber dispensing cartridge refilling device according to an additional embodiment of the invention and taken along lines 23—23 of FIG. 24.
Figure 24:
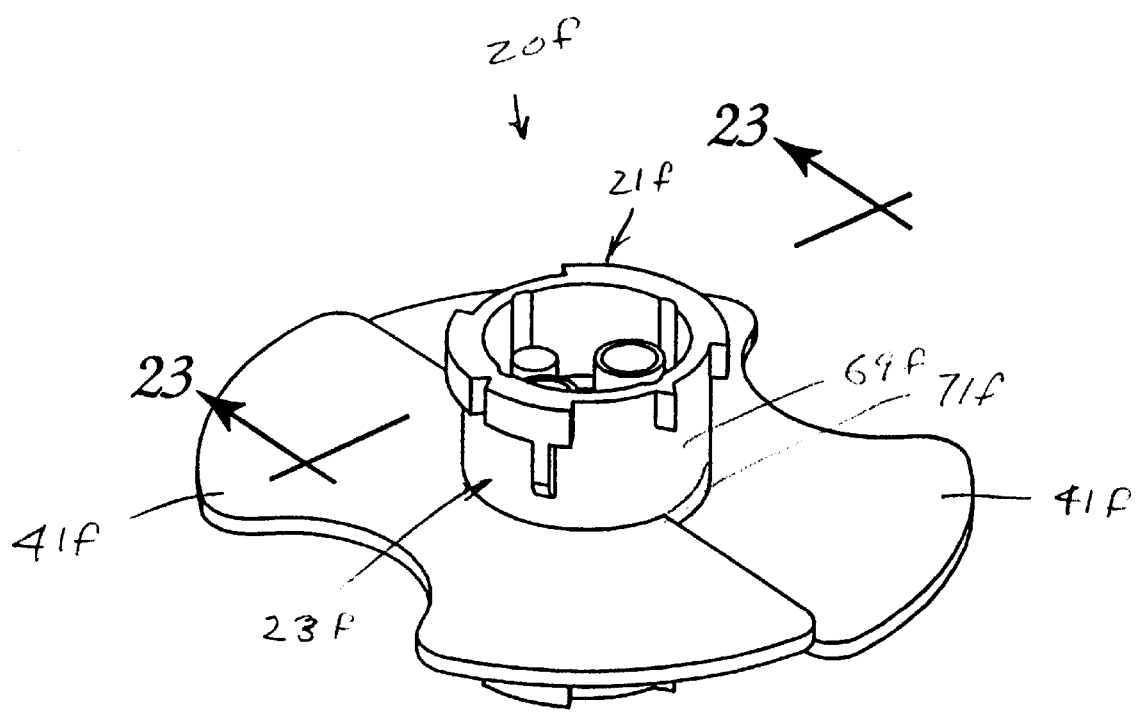
FIG. 24 is a perspective view of the refilling device shown in FIG. 23.

A dual chamber dispensing cartridge refilling device 20f according to yet another embodiment of the invention is shown in FIGS. 23 and 24. Except as described below, the construction and use of the refilling device 20f is essentially identical to the construction and use of the refilling device 20e described in connection with FIGS. 16–22.

The refilling device 20f has a retainer 21f which includes a central, cylindrical hollow member 23f having a first part 69f and a separate, second part 71f. Each of the parts 69f, 71f are identical and connected to a coupler that includes flanges, projections and stops similar to the flanges 34e, projections 66e and stops 68e described above. Each of the parts 69f, 71f is fixedly connected to a respective handle or arm 41f that has a curved outer edge section with a finger engagable notch or recess.

The refilling device 20f also includes an adapter body 22f that is somewhat similar to the body 22e, except that the body 22f includes a pair of spaced apart, annular plates 25f. Each of the plates 25f contacts an inner, circular shoulder presented by a respective, adjacent part 69f, 71f. As can be appreciated by comparison of FIG. 23 to FIG. 18, both the retainer 21f and the adapter body 22f are somewhat longer in directions along their central axis in comparison to the lengths of the retainer 21e and adapter body 22e.

Use of the refilling device 20f is somewhat similar to the use of the refilling device 20e. However, the two parts 69f, 71f may each be independently moved relative to the adapter body 22f. As a consequence, the refilling device 20f may be locked onto one cartridge before being connected with a second cartridge, and may also be independently released from only one cartridge as desired. Such construction is advantageous in certain instances, as for example when a series of partially empty cartridges are sequentially connected to the refilling device 20f in order to consolidate all remaining materials in a single host cartridge.

Figure 25:
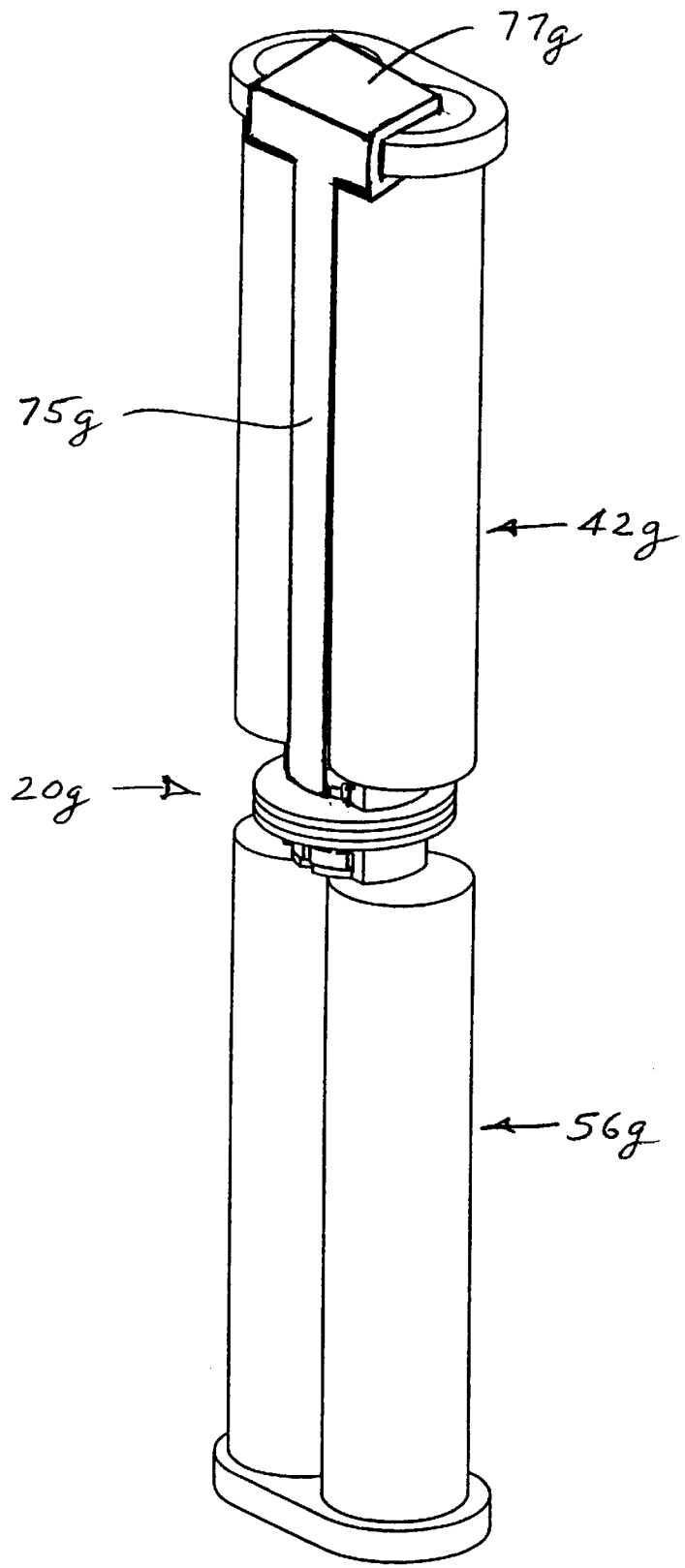
FIG. 25 is a view somewhat similar to FIG. 22 but showing a refilling device according to another embodiment of the invention.

FIG. 25 shows another embodiment of the invention, wherein a refilling device 20g is releasably coupled to a pair of dual chamber dispensing cartridges 42g, 56g. The cartridges 42g, 56g are identical to the cartridges 42e, 56e shown in FIG. 22. The refilling device 20g is essentially identical to the refilling device 20e illustrated in FIGS. 16–18, except for the differences that are set out below.

The refilling device 20 includes an elongated support arm 75g that is fixed directly to one end of the adapter body (not shown, but otherwise identical to the adapter body 22e). The arm 75g includes an outer clip 77g that preferably has a generally "U"-shaped configuration to extend over the rear face of the rear flange of the cartridge 42g as well as across an adjacent portion of the front face of the rear flange of the cartridge 42g. Preferably, an inner wall section of the outer portion of the clip 77g includes a pair of spaced apart bumps or protrusions (not shown) that extend slightly into the openings of the cartridge chambers to aid in retention.

The arm 75g functions as a first coupler to releasably connect the cartridge 42g to the device 20g. Optionally, the arm 75g is resilient and can be deflected laterally by finger pressure to facilitate placing the cartridge outlets over respective projections of the device 20g for communication with the passages of the device 20g. As another option, the arm 75g is relatively rigid, and the projections of the device 20g are shortened in order to facilitate coupling of the arm 75g to the cartridge 42g. Preferably, the length of the outer section of the clip 77g is sufficient to extend past the center of the cartridge chamber openings to help ensure that the pistons in the chamber do not cock.

Additionally, the refilling device 20g lacks flanges, stops and a projection on its end that faces the cartridge 42g. However, the refilling device 20g has a second coupler that is identical to the second coupler 32e described above, and includes flanges, stops and a projection similar to the flanges 34e, stops 68e and projection 66e described above.

Once the cartridge 42g is connected to the device 20g, a second cartridge 56g is advanced toward the device 20g in an orientation sufficient to move the projections adjacent the second coupler into the respective outlets of the cartridge 56g. The cartridge 56g is secured to the device 20g by rotating the disk-shaped handle that is similar to the handle 41e mentioned above. Such turning movement of the handle brings the tabs of the cartridge 56g into snug, interconnected engagement with the flanges of the second coupler.

Preferably, the arm 75g includes a tab (not shown) that fits into a notch on one side of the rear flange of the cartridge 42g (see, e.g., the notch of the rear flange on the cartridge 42e illustrated in FIG. 22). That notch ensures that the outlets of the cartridge 42g are communicating with the proper passages of the device 20g when the latter is connected to the cartridge 42g. Optionally, the clip 77g may be provided with a roughened surface or knurled edge to facilitate uncoupling, or the arm 75g may be provided with a handle or tab for the same purpose. As other alternatives, the arm 75g may be provided in different lengths or be adjustable in length in order to fit cartridges of various sizes.

Figure 26:
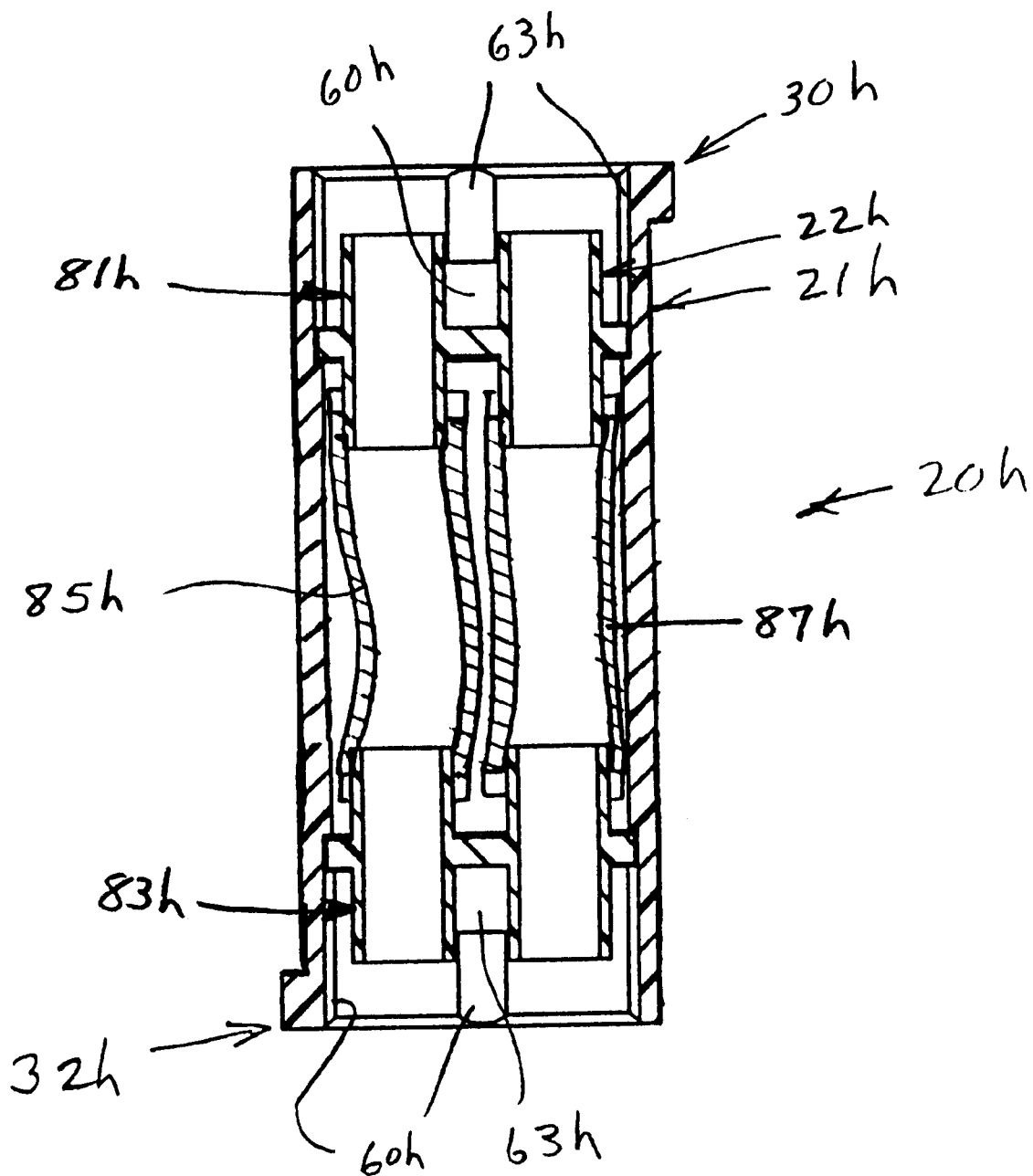
FIG. 26 is a view somewhat similar to FIG. 25 but showing a refilling device according to still another embodiment of the invention.

Another embodiment of the invention is shown in FIG. 26, wherein a refilling device 20h includes a retainer 21h as well as an inner adapter body 22h. The retainer 21h includes a hollow member with a generally cylindrical configuration with a first coupler 30h and a second coupler 32h located on opposite ends. Each of the couplers 30h, 32h includes flanges, stops and a projection similar to the flanges 34e, stops 68e and projection 66e as described above.

The adapter body 22h includes a first section 81h and a second section 83h located adjacent the couplers 30h, 32h respectively. The adapter section 81h is optionally identical to the adapter body 22e, and the adapter section 83h is also optionally identical to the adapter body 22e. Both of the adapter sections 81h, 83h are slidably received in respective, spaced apart circular grooves that extend around the inner wall surface of the retainer 21h.

A length of flexible tubing 85h is joined to one of the projections of each of the adapter sections 81h, 83h in order to communicate a first passage of each section 81h, 83h. Similarly, a second length of flexible tubing 87h is connected to the remaining, facing projection of each adapter section 81h, 83h in order to communicate the remaining passages of the sections 81h, 83h. The length of the tubing 85h, 87h may be longer or shorter than that shown as may be desirable in use in the manner set out below.

The refilling device 20h is used by advancing a dual chamber dispensing cartridge such as the cartridges 42e, 56e toward the device 20h in order to move the outlets of the cartridge to a position of surrounding the facing projections of the adapter section 81h. The retainer 21e may then be rotated about its central axis relative to the cartridge in order to releasably lock the first coupler 30h into secure connection with the first cartridge. Next, a second dispensing cartridge is advanced toward the projections of the adapter section 83h in a similar manner. Once the outlets of the second cartridge are placed in a position surrounding to respective projections of the adapter section 83h, either the retainer 21h or the first cartridge may be grasped and turned relative to the second cartridge in order to enable the second coupler 32h to releasably lock the second cartridge to the refilling device 30h. As the adapter sections 81h, 83h rotate relative to the retainer 21h, the tubings 85h, 87h twist as may be needed.

Preferably, and as shown in FIG. 26, the refilling device 20h has snap-action elements 60h and associated recesses 63h that are associated with each adapter section 81h, 83h. Such elements 60h and recesses 63h are similar in construction and function to the elements 60e and recesses 63e set out above.

As an alternative, the adapter sections 81h, 83h and the tubings 85h, 87h may be replaced by a single unitary body having flexible tubing-like sections that are sufficiently flexible to twist and enable the adapter to pivot at least ninety degrees relative to the retainer 21h. Preferably, however, ends of the tubing-like sections are sufficiently rigid to avoid deformation when pushed into the outlets of a dispensing cartridge. As another alternative, the flanges, stops and projection of the first coupler 30h may be eliminated and replaced with an arm and clip similar to the arm 75g and clip 77g illustrated in FIG. 25.

Those skilled in the art may recognize that a variety of modifications, additions or alterations may be made to the currently preferred embodiments described in detail above without departing from the spirit of our invention. For example, the retainers and adapters may have other configurations to match other types of dispensing cartridges. Additionally, the coupling structure used to couple the cartridges 42, 56 to the refilling device may be constructed other than that which is shown by latching to other elements of the cartridges, or by using a housing that encloses both cartridges as well as the refilling device. As another alternative, the couplers may be provided as part of the cartridges and also used for connection to static mixers, so that a separate part that includes couplers such as a retainer (e.g., retainer 21a) would be unnecessary and only the body with the two passageways need be installed in the cartridge outlets before coupling the cartridges together. A number of other variations are also possible. Accordingly, the scope of the invention should not be deemed limited to the structure described above in detail, but instead only by a fair reading of the claims which follow along with their equivalents.

We claim:

1. A device for at least partially refilling a dual chamber dispensing cartridge with a composition from a second dual chamber dispensing cartridge comprising:

a body having a pair of side-by-side passages; and a retainer movably connected to said body, said retainer including a member and a first coupler connected to said member for releasably coupling said body to a first dual chamber dispensing cartridge in an orientation wherein said passages are in communication with side-by-side outlets of the first cartridge, said retainer also including a second coupler connected to said member for releasably coupling said body to a second dual chamber dispensing cartridge in an orientation wherein said passages are in communication with side-by-side outlets of the second cartridge, said member being movable relative to said body between a first position wherein said first coupler has coupled said body to the first cartridge and a second position wherein said body may be released from the first cartridge, said device including at least one snap-action element associated with at least one of said body and said retainer that releasably retains said member in at least one of said positions.

2. The device of claim 1, wherein said body has a generally cylindrical shape, and wherein said first coupler and said second coupler include flanges for releasable connection to the first cartridge and the second cartridge respectively.

3. The device of claim 2, wherein said device includes a hollow cylindrical member connected to said first coupler and said second coupler, and wherein said body is received in said cylindrical member.

4. The device of claim 3, wherein said body is rotatably connected to said cylindrical member.

5. The device of claim 3, wherein said device includes structure for retaining said body in said member.

6. The device of claim 3, wherein said member is integrally connected to said flanges of said first coupler and said second coupler.

7. The device of claim 5, wherein said second coupler couples said body to the second cartridge when said member is in said first position and said body may be released from said second cartridge when said member is in said second position.

8. The device of claim 1, wherein said at least one snap-action element is fixed to said body and wherein said retainer includes at least one recess for receiving said at least one snap-action element.

9. The device of claim 1 including an orienting section for preventing one of said passages from being placed in communication with a certain one of the outlets of the first cartridge and the second cartridge.

10. The device of claim 1, wherein said body, said first coupler and said second coupler are integrally molded of a plastic material.

11. A device of claim 1, wherein said device includes at least one outwardly extending handle connected to said retainer.

12. The device of claim 2 including at least one outwardly extending arm for facilitating rotation of said member relative to one of the first cartridge and the second cartridge.

13. The device of claim 1, wherein said first coupler includes an arm for contact with a rear flange of the first cartridge.

14. The device of claim 1 wherein said body includes a first section and a second section each presenting a portion of the length of said passages, and wherein said portions of said passages are interconnected by lengths of flexible tubing.

15. A device for at least partially refilling a dual chamber dispensing cartridge with a composition from a second dual chamber dispensing cartridge comprising:

a body having a pair of side-by-side passages;

a first coupler for releasably coupling said body to a first dual chamber dispensing cartridge in an orientation wherein said passages are in communication with side-by-side outlets of the first cartridge; and a second coupler for releasably coupling said body to a second dual chamber dispensing cartridge in an orientation wherein said passages are in communication with side-by-side outlets of the second cartridge, said body also including at least two sealing sections for sealing contact with the first cartridge and the second cartridge when the first cartridge and the second cartridge are coupled by said first coupler and said second coupler to said body.

16. The device of claim 15, wherein said body has a generally cylindrical shape, and wherein said first coupler and said second coupler include flanges for releasable connection to the first cartridge and the second cartridge respectively.

17. The device of claim 16, wherein said device includes a hollow cylindrical member connected to said first coupler and said second coupler, and wherein said body is received in said cylindrical member.

18. The device of claim 17, wherein said body is rotatably connected to said cylindrical member.

19. The device of claim 17, wherein said device includes structure for retaining said body in said member.

20. The device of claim 17, wherein said member is integrally connected to said flanges of said first coupler and said second coupler.

21. The device of claim 19, wherein said body is non-releasably retained in said member.

22. The device of claim 16 including at least one outwardly extending arm for facilitating rotation of said member relative to one of the first cartridge and the second cartridge.

23. The device of claim 15, wherein said first coupler and said second coupler include outwardly extending, flexible legs for releasable connection to the first cartridge and the second cartridge respectively.

24. The device of claim 23, wherein each of said legs includes a hook.

25. The device of claim 15, wherein said first coupler and said second coupler include a generally U-shaped retainer with at least two pairs of outwardly extending flanges.

26. The device of claim 15 including an orienting section for preventing one of said passages from being placed in communication with a certain one of the outlets of the first cartridge and the second cartridge.

27. The device of claim 15, wherein said body, said first coupler and said second coupler are integrally molded of a plastic material.

28. The device of claim 15, wherein said body has a generally hollow interior with a dividing wall presenting said side-by-side passages.

29. The device of claim 15, wherein said first coupler and said second coupler include flanges for releasable connection to the first cartridge and the second cartridge respectively.

* * * * *